(12) United States Patent
Shibuya et al.

(10) Patent No.: US 11,271,162 B2
(45) Date of Patent: Mar. 8, 2022

(54) FULLERENE DERIVATIVES, AND ORGANIC PHOTOELECTRIC DEVICE, IMAGE SENSOR, AND ELECTRONIC DEVICE INCLUDING THE SAME

(71) Applicant: Samsung Electronics Co., Ltd., Suwon-si (KR)

(72) Inventors: Hiromasa Shibuya, Suwon-si (KR); Yeong Suk Choi, Suwon-si (KR); Yutaka Matsuo, Tokyo (JP)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/685,263

(22) Filed: Nov. 15, 2019

(65) Prior Publication Data
US 2020/0161557 A1 May 21, 2020

(30) Foreign Application Priority Data
Nov. 16, 2018 (KR) .................. 10-2018-0141753

(51) Int. Cl.
*H01L 51/00* (2006.01)
*C07C 321/28* (2006.01)
(Continued)

(52) U.S. Cl.
CPC ........ *H01L 51/0047* (2013.01); *C07C 321/28* (2013.01); *H01L 27/14647* (2013.01);
(Continued)

(58) Field of Classification Search
CPC ............. H01L 51/0047; H01L 51/0036; H01L 51/0043; H01L 51/4253; C07C 13/62; C07C 2604/00; Y02E 10/549
See application file for complete search history.

(56) References Cited

U.S. PATENT DOCUMENTS

| 10,319,914 B2* | 6/2019 | Morse ................. H01L 51/0036 |
| 2017/0062739 A1 | 3/2017 | Choi et al. |
| 2017/0294585 A1 | 10/2017 | Morse et al. |

FOREIGN PATENT DOCUMENTS

| JP | 2007-206240 A | 8/2007 |
| JP | 2016-075739 A | 5/2016 |

(Continued)

OTHER PUBLICATIONS

P. E. Burrows et al, "Relationship between electroluminescence and current transport in organic heterojunction lightemitting devices" J. Appl. Phys. 79, 7991 (1996); doi: 10.1063/1.362350.
(Continued)

*Primary Examiner* — Matthew T Martin
(74) *Attorney, Agent, or Firm* — Harness, Dickey & Pierce, P.L.C.

(57) ABSTRACT

Disclosed are a fullerene derivative including a substituent represented by Chemical Formula 1, and an organic photoelectric device, an image sensor, and an electronic device including the same.

[Chemical Formula 1]

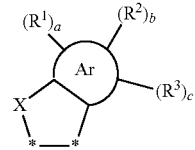

In Chemical Formula 1, X, Ar, $R^1$ to $R^3$, a, b, and c are the same as defined in the detailed description.

27 Claims, 9 Drawing Sheets

(51) Int. Cl.
  *H01L 27/146* (2006.01)
  *H01L 27/28* (2006.01)
  *H01L 27/30* (2006.01)
  *H01L 51/42* (2006.01)
  *H01L 51/44* (2006.01)

(52) U.S. Cl.
  CPC .......... *H01L 27/286* (2013.01); *H01L 27/307* (2013.01); *H01L 51/4253* (2013.01); *H01L 51/442* (2013.01)

(56) References Cited

FOREIGN PATENT DOCUMENTS

| KR | 10-2016-0042314 A | 4/2016 |
| KR | 10-2017-0024545 A | 3/2017 |
| KR | 10-2017-0047370 A | 5/2017 |
| WO | WO-2015/149905 A1 | 10/2015 |

OTHER PUBLICATIONS

Takahiro Kusukawa et al, "Photochemical functionalizations of C60 with phenylpolysilanes" Journal of Organometallic Chemistry 559 (1998) 11-22, Jan. 20, 1998.

D.V. Konarev et al., 'Donor-acceptor interaction of fullerene $C_{60}$ with triptycene in molecular complex TPC•$C_{60}$' *Journal of Molecular Structure*, vol. 526, 2000, pp. 25-29.

Extended European Search Report dated Mar. 24, 2020, issued in corresponding European Patent Application No. 19209654.3.

Adam D. Darwish et al., 'Electrophilic substitution of $C_{60}F_{18}$ into phenols: HF elimination between OH and a 1,3-shifted flourine giving benzofurano[2',3':10,26]hexadecafluoro[60]fullerene and derivatives' *Org. Biomol. Chem.*, vol. 1, 2003, pp. 1764-1768.

Yutaka Matsuo et al., 'Fullerene cation-mediated demethylation/cyclization to give 5- and 7-membered cyclo[60] fullerene derivatives' *J. Mater. Chem. A*, vol. 5, 2017, pp. 2774-2783.

Y. Numata et al., 'Substituent Effect on the Reduction Potentials of Heterocyclic-fused [60] Fullerene Derivatives' *ECS Transactions*, vol. 16, No. 47, 2009, pp. 33-43.

Masakazu Nambo et al., 'Aziridinofullerene: A Versatile Platform for Functionalized Fullerenes' *Journal of the American Chemistry Society*, vol. 133, 2011, pp. 2402-2405.

Adam D. Darwish et al., 'Novel base-catalysed formation of benzo[b]furano[60]- and -[70]fullerenes' *J. Chem. Soc.*, Perkin Trans. 2, 1999, pp. 1983-1988.

Yutaka Matsuo et al., 'Synthesis of Benzothieno[60]fullerenes through Fullerenyl Cation Intermediates' *J. Org. Chem.*, vol. 84, 2019, pp. 6270-6277.

\* cited by examiner

FULLERENE DERIVATIVES, AND ORGANIC PHOTOELECTRIC DEVICE, IMAGE SENSOR, AND ELECTRONIC DEVICE INCLUDING THE SAME

CROSS-REFERENCE TO RELATED APPLICATION

This application claims the benefit of priority from Korean Patent Application No. 10-2018-0141753 filed in the Korean Intellectual Property Office on Nov. 16, 2018, the entire contents of which are incorporated herein by reference.

BACKGROUND

1. Field

Example embodiments relate to fullerene derivative and an organic photoelectric device, an image sensor, and an electronic device including the same are disclosed.

2. Description of the Related Art

Fullerene has a closed-cage structure made of carbon and has been used in various fields because of stable structures and good electrical properties. Recently, various fullerene derivatives having substituents have been developed.

The photoelectric device is a device that converts light into an electric signal using a photoelectric effect, and includes a photodiode and an optical transistor, and may be applied to an electronic device such as an image sensor. The photoelectric device may include a fullerene or a derivative having high light absorption characteristics and good electrical characteristics.

SUMMARY

An example embodiment provides a novel fullerene derivative that may be applied to a photoelectric device.

Another example embodiment provides an organic photoelectric device including the fullerene derivative.

Another example embodiment provides an image sensor and an electronic device including the organic photoelectric device.

According to an example embodiment, a fullerene derivative including a substituent represented by Chemical Formula 1 is provided.

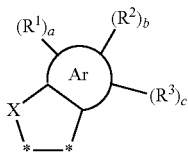

[Chemical Formula 1]

In Chemical Formula 1,

X is S,

Ar is a C6 to C30 aromatic ring, $R^1$ to $R^3$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, a substituted or unsubstituted C6 to C30 aryl group, a substituted or unsubstituted C3 to C30 cycloalkyl group, a substituted or unsubstituted C3 to C30 heterocyclic group, a halogen, a cyano group, or a combination thereof, a, b, and c are independently an integer of 1 to 3, provided that a+b+c does not exceed a valence of Ar, and

*—* is a linking portion with a fullerene core.

In some embodiments, in Chemical Formula 1, at least one of $R^1$ to $R^3$ may be a linear substituent, a branched substituent, or a cyclic substituent. The linear substituent may be selected from a substituted or unsubstituted C1 to C20 linear alkyl group, a substituted or unsubstituted C2 to C20 linear alkenyl group, a substituted or unsubstituted C2 to C20 linear alkynyl group, a substituted or unsubstituted C1 to C20 linear heteroalkyl group, a substituted or unsubstituted C2 to C20 linear heteroalkenyl group, a substituted or unsubstituted C2 to C20 linear heteroalkynyl group, or a combination thereof. The branched substituent may be selected from a substituted or unsubstituted C3 to C20 branched alkyl group, a substituted or unsubstituted C3 to C20 branched alkenyl group, a substituted or unsubstituted C3 to C20 branched alkynyl group, a substituted or unsubstituted C3 to C20 branched heteroalkyl group, a substituted or unsubstituted C3 to C20 branched heteroalkenyl group, a substituted or unsubstituted C3 to C20 branched heteroalkynyl group, or a combination thereof. The cyclic substituent may be selected from a substituted or unsubstituted C6 to C30 aryl group, a substituted or unsubstituted C3 to C30 cycloalkyl group, a substituted or unsubstituted C3 to C30 heterocyclic group, or a combination thereof.

In some embodiments, in Chemical Formula 1, at least two of $R^1$ to $R^3$ may be a linear substituent, a branched substituent, or a cyclic substituent. The linear substituent may be selected from a substituted or unsubstituted C1 to C20 linear alkyl group, a substituted or unsubstituted C2 to C20 linear alkenyl group, a substituted or unsubstituted C2 to C20 linear alkynyl group, a substituted or unsubstituted C1 to C20 linear heteroalkyl group, a substituted or unsubstituted C2 to C20 linear heteroalkenyl group, a substituted or unsubstituted C2 to C20 linear heteroalkynyl group, or a combination thereof. The branched substituent may be selected from a substituted or unsubstituted C3 to C20 branched alkyl group, a substituted or unsubstituted C3 to C20 branched alkenyl group, a substituted or unsubstituted C3 to C20 branched alkynyl group, a substituted or unsubstituted C3 to C20 branched heteroalkyl group, a substituted or unsubstituted C3 to C20 branched heteroalkenyl group, a substituted or unsubstituted C3 to C20 branched heteroalkynyl group, or a combination thereof. The cyclic substituent may be selected from a substituted or unsubstituted C6 to C30 aryl group, a substituted or unsubstituted C3 to C30 cycloalkyl group, a substituted or unsubstituted C3 to C30 heterocyclic group, or a combination thereof.

In some embodiments, at least one of $R^1$ to $R^3$ may be the linear substituent and at least one of $R^1$ to $R^3$ may be the branched substituent or the cyclic substituent.

In some embodiments, at least one of $R^1$ to $R^3$ may be the branched substituent and at least one of $R^1$ to $R^3$ may be the cyclic substituent.

In some embodiments, the substituted or unsubstituted C3 to C20 branched alkyl group, the substituted or unsubstituted C3 to C20 branched alkenyl group, and the substituted or unsubstituted C3 to C20 branched alkynyl group may be represented by Chemical Formula 1-1.

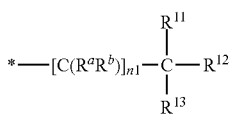
[Chemical Formula 1-1]

In Chemical Formula 1-1, $R^a$ and $R^b$ is hydrogen, a halogen, a cyano group, or C1 to C6 alkyl group, n1 is an integer of 0 to 10, and $R^{11}$ to $R^{13}$ is hydrogen, a halogen, a cyano group, a C1 to C10 alkyl group, a C1 to C10 alkoxy group, a C2 to C10 alkenyl group, or a C2 to C10 alkynyl group, provided that at least two of $R^{11}$ to $R^{13}$ are a C1 to C10 alkyl group, a C1 to C10 alkoxy group, a C2 to C10 alkenyl group, or a C2 to C10 alkynyl group.

In some embodiments, the C3 to C20 branched heteroalkyl group, C3 to C20 branched heteroalkenyl group, and C3 to C20 branched heteroalkynyl group may be a functional group including —O—, —S—, —S(=O)—, —S(=O)$_2$—, —C(=O)—, —C(=O)O—, —OC(=O)—, or a combination thereof, instead of at least one —C($R^c R^d$)— in Chemical Formula 1-2 (that is, a functional group obtained by replacing at least one —C($R^c R^d$)— in Chemical Formula 1-2 with —O—, —S—, —S(=O)—, —S(=O)$_2$—, —C(=O)—, —C(=O)O—, —OC(=O)—, or a combination thereof). When the number of the replaced —C($R^c R^d$)— is greater than or equal to 2, these replaced —C($R^c R^d$)— are not adjacent to each other.

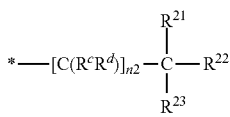
[Chemical Formula 1-2]

In Chemical Formula 1-2, $R^c$ and $R^d$ is hydrogen, a halogen, a cyano group, a C1 to C6 alkyl group, a C1 to C6 alkoxy group, a C2 to C10 ether group, or a C2 to C10 ester group, n2 is an integer of 2 to 10, and $R^{21}$ to $R^{23}$ are hydrogen, a halogen, a cyano group, a C1 to C10 alkyl group, a C1 to C10 alkoxy group, a C2 to C10 alkenyl group, or a C2 to C10 alkynyl group, provided that at least two of $R^{11}$ to $R^{13}$ are a C1 to C10 alkyl group, a C1 to C10 alkoxy group, a C2 to C10 alkenyl group, or a C2 to C10 alkynyl group.

In Chemical Formula 1, Ar may be a benzene ring or a fused aromatic ring, and for example Ar may be a naphthalene ring, an anthracene ring, a phenanthrene ring, a pyrene ring, or a triphenylene ring.

In some embodiments, the fullerene derivative may exhibit a reversible peak in the current-voltage curve line of cyclic-voltammetry (CV). Such a reversible peak means that electrical properties are stable. In case that such a behavior is irreversible, possibility of decomposition during driving of the device may increase.

In some embodiments, the fullerene derivative may exhibit three or more reduction peaks at −1.0 V to −2.0 V in the current-voltage curve line of cyclic-voltammetry (CV).

In some embodiments, the fullerene derivative may have a LUMO energy level of about 2.6 eV to about 4.1 eV and a HOMO energy level of about 5.5 eV to about 6.9 eV. The fullerene derivative may have an energy bandgap of 2.46 eV to about 2.56 eV.

In some embodiments, the fullerene derivative may be a compound capable of being vacuum-deposited by sublimation.

In some embodiments, a temperature at which a weight loss of 10 wt % relative to an initial weight of the fullerene derivative occurs at less than or equal to about 0.1 Pa during a thermogravimetric analysis may be less than or equal to about 460° C., and a temperature at which 50 wt % weight loss occurs relative to an initial weight of the fullerene derivative may be less than or equal to about 500° C. during a thermogravimetric analysis.

In some embodiments, the substituent represented by Chemical Formula 1 may be represented by one of Chemical Formulae 2A to 4A.

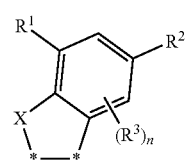
[Chemical Formula 2A]

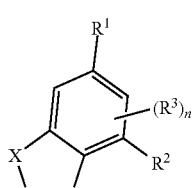
[Chemical Formula 2B]

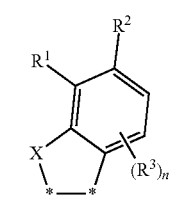
[Chemical Formula 3A]

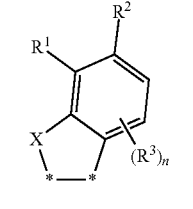
[Chemical Formula 3B]

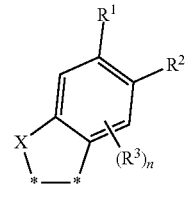
[Chemical Formula 3C]

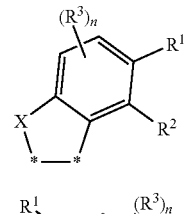
[Chemical Formula 4A]

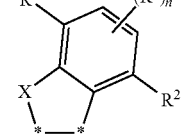

In Chemical Formulae 2A to 4A,

X is S, $R^1$ to $R^3$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, a substituted or unsubstituted C6 to C30 aryl group, a substituted or unsubstituted C3 to C30 cycloalkyl group, a substituted or unsubstituted C3 to C30 heterocyclic group, a halogen, a cyano group, or a combination thereof, n is an integer of 1 or 2, and

*—* is a linking point with a fullerene core.

In some embodiments, in Chemical Formulae 2A to 4A, at least one of $R^1$ and $R^2$ may be a linear substituent selected from a substituted or unsubstituted C1 to C20 linear alkyl group, a substituted or unsubstituted C2 to C20 linear alkenyl group, a substituted or unsubstituted C2 to C20 linear alkynyl group, a substituted or unsubstituted C1 to C20 linear heteroalkyl group, a substituted or unsubstituted C2 to C20 linear heteroalkenyl group, a substituted or unsubstituted C2 to C20 linear heteroalkynyl group, or a combination thereof.

In some embodiments, in Chemical Formulae 2A to 4A, at least one of $R^1$ and $R^2$ may be a branched substituent selected from a substituted or unsubstituted C3 to C20 branched alkyl group, a substituted or unsubstituted C3 to C20 branched alkenyl group, a substituted or unsubstituted C3 to C20 branched alkynyl group, a substituted or unsubstituted C3 to C20 branched heteroalkyl group, a substituted or unsubstituted C3 to C20 branched heteroalkenyl group, a substituted or unsubstituted C3 to C20 branched heteroalkynyl group, or a combination thereof.

In some embodiments, in Chemical Formulae 2A to 4A, at least one of $R^1$ and $R^2$ may be a cyclic substituent selected from a substituted or unsubstituted C6 to C30 aryl group, a substituted or unsubstituted C3 to C30 cycloalkyl group, a substituted or unsubstituted C3 to C30 heterocyclic group, or a combination thereof.

In some embodiments, in Chemical Formulae 2A to 4A, one of $R^1$ and $R^2$ may be the linear substituent and the other of $R^1$ and $R^2$ may be the branched substituent or the cyclic substituent.

In some embodiments, in Chemical Formulae 2A to 4A, one of $R^1$ and $R^2$ may be the branched substituent and the other of $R^1$ and $R^2$ may be the cyclic substituent.

In some embodiments, the substituent represented by Chemical Formula 1 may be represented by one of Chemical Formulae 5A to 7B.

[Chemical Formula 5A]

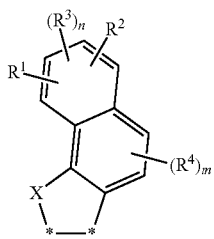

[Chemical Formula 5B]

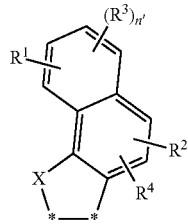

[Chemical Formula 6A]

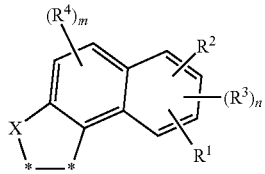

[Chemical Formula 6B]

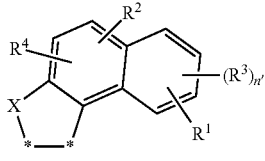

[Chemical Formula 7A]

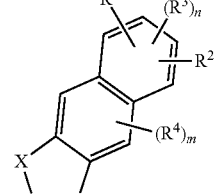

[Chemical Formula 7B]

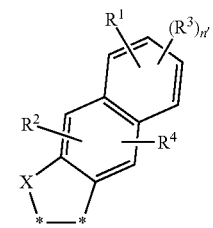

In Chemical Formulae 5A to 7B,

X is S, $R^1$ to $R^4$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, a substituted or unsubstituted C6 to C30 aryl group, a substituted or unsubstituted C3 to C30 cycloalkyl group, a substituted or unsubstituted C3 to C30 heterocyclic group, a halogen, a cyano group, or a combination thereof, n and m are independently an integer of 1 or 2, n' is an integer of 1 to 3, and

*—* is a linking point with a fullerene core.

In some embodiments, in Chemical Formulae 5A to 7B, at least one of $R^1$ and $R^2$ may be a linear substituent selected from a substituted or unsubstituted C1 to C20 linear alkyl group, a substituted or unsubstituted C2 to C20 linear alkenyl group, a substituted or unsubstituted C2 to C20 linear alkynyl group, a substituted or unsubstituted C1 to C20 linear heteroalkyl group, a substituted or unsubstituted C2 to C20 linear heteroalkenyl group, a substituted or unsubstituted C2 to C20 linear heteroalkynyl group, or a combination thereof.

In some embodiments, in Chemical Formulae 5A to 7B, at least one of $R^1$ and $R^2$ may be a branched substituent selected from a substituted or unsubstituted C3 to C20 branched alkyl group, a substituted or unsubstituted C3 to C20 branched alkenyl group, a substituted or unsubstituted C3 to C20 branched alkynyl group, a substituted or unsubstituted C3 to C20 branched heteroalkyl group, a substituted or unsubstituted C3 to C20 branched heteroalkenyl group, a substituted or unsubstituted C3 to C20 branched heteroalkynyl group, or a combination thereof.

In some embodiments, in Chemical Formulae 5A to 7B, at least one of $R^1$ and $R^2$ may be a cyclic substituent selected from a substituted or unsubstituted C6 to C30 aryl group, a substituted or unsubstituted C3 to C30 cycloalkyl group, a substituted or unsubstituted C3 to C30 heterocyclic group, or a combination thereof.

In Chemical Formulae 5A to 7B, at least one of $R^1$ and $R^2$ may be the linear substituent and the other of $R^1$ and $R^2$ may be the branched substituent or the cyclic substituent.

In some embodiments, in Chemical Formulae 5A to 7B, at least one of $R^1$ and $R^2$ may be the branched substituent and the other of $R^1$ and $R^2$ may be the cyclic substituent.

In some embodiments, the fullerene core may be C60, C70, C74, C76, or C78.

According to another embodiment, a thin film includes the fullerene derivative.

In some embodiments, an extinction coefficient at a 450 nm wavelength of the thin film may be smaller than an extinction coefficient at a 450 nm wavelength of a thin film including unsubstituted fullerene.

In some embodiments, an absorption coefficient at a 450 nm wavelength of the thin film may be less than or equal to about ½ of an absorption coefficient at a 450 nm wavelength of a thin film including unsubstituted fullerene.

Another embodiment provides an organic photoelectric device including a first electrode and a second electrode facing each other and an organic layer disposed between the first electrode and the second electrode, wherein the organic layer includes the fullerene derivative represented by Chemical Formula 1.

In some embodiments, an organic layer may include an active layer and the active layer may include a p-type semiconductor and an n-type semiconductor to form a pn junction, wherein the n-type semiconductor includes the aforementioned fullerene derivative.

According to another example embodiment, an image sensor including the organic photoelectric device is provided.

According to another example embodiment, an electronic device including the image sensor is provided.

According to another example embodiment, an electronic device including the organic photoelectric device is provided.

The fullerene derivatives having excellent optical properties and electrical characteristics may improve characteristics of organic photoelectric devices, image sensors, and electronic devices including the same.

DETAILED DESCRIPTION

Figure 1:
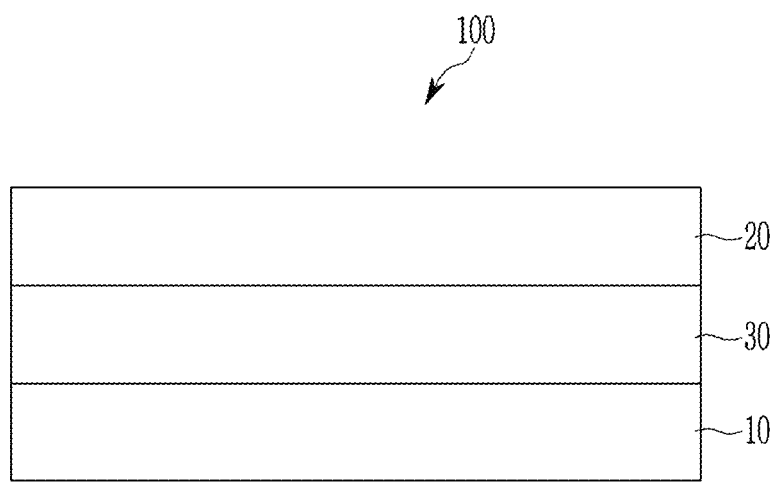
FIG. 1 is a cross-sectional view showing an organic photoelectric device according to an embodiment.

Hereinafter, example embodiments of the present disclosure will be described in detail so that a person skilled in the art would understand the same. This disclosure may, however, be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same or similar reference numeral throughout the specification.

Hereinafter, "combination" includes mixtures, inter-mutual substitution and stack structures of two or more.

As used herein, when a definition is not otherwise provided, "substituted" refers to replacement of hydrogen of a compound or a functional group by a substituent selected from a halogen, a hydroxy group, a nitro group, a cyano group, an amino group, an azido group, an amidino group, a hydrazino group, a hydrazono group, a carbonyl group, a carbamyl group, a thiol group, an ester group (—COOR, wherein is a C1 to C20 alkyl group), a carboxyl group or a salt thereof, sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, "hetero" refers to one including one to three heteroatoms selected from N, O, S, P, and Si, and remaining carbons in one compound, functional group, or moiety.

As used herein, when a definition is not otherwise provided, "aryl group" refers to a group including at least one aromatic hydrocarbon moiety, for example a single aromatic hydrocarbon moiety in which all the ring-forming elements of the aromatic hydrocarbon moiety having p-orbitals which form conjugation such as a phenyl group or a naphthyl group; two or more hydrocarbon aromatic moieties linked by a sigma bond such as a biphenyl group, a terphenyl group, or a quaterphenyl group; and two or more aromatic hydrocarbon moieties fused directly or indirectly to provide a non-aromatic fused ring such as a fluorenyl group.

As used herein, when a definition is not otherwise provided, "heterocyclic group" is a generic concept of a C2 to C30 (e.g., C2 to C20) heteroaryl group, a C2 to C30 (e.g., C2 to C20) heterocycloalkyl group or a fused ring thereof, and may include at least one heteroatom instead of carbon (C) in a ring such as an aryl group, a cycloalkyl group, a fused ring thereof, or a combination thereof wherein the heteroatom may be for example N, O, S, P, and/or Si, but is not limited thereto. When the heterocyclic group is a fused ring, at least one heteroatom may be included in an entire ring or each ring of the heterocyclic group.

As used herein, when a definition is not otherwise provided, "heteroaryl group" refers to an aryl group including at least one heteroatom, wherein the heteroatom may be for example N, O, S, P, and/or Si, but is not limited thereto. At least two heteroaryl groups may be linked directly through a sigma bond, at least two heteroaryl groups may be fused with each other, or at least one heteroaryl group may be fused with at least one heteroalkyl group. When the heteroaryl group is a fused ring, each ring may include one to three heteroatoms.

Hereinafter, a fullerene derivative according to an embodiment is described.

A fullerene derivative according to an embodiment may be represented by Chemical Formula 1.

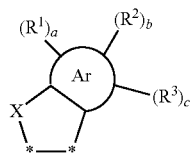

[Chemical Formula 1]

In Chemical Formula 1,

X is S,

Ar is a C6 to C30 aromatic ring, $R^1$ to $R^3$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, a substituted or unsubstituted C6 to C30 aryl group, a substituted or unsubstituted C3 to C30 cycloalkyl group, a substituted or unsubstituted C3 to C30 heterocyclic group, a halogen, a cyano group, or a combination thereof, a, b, and c are independently an integer of 1 to 3, and

*—* is a linking point with a fullerene core.

In Chemical Formula 1, a, b, and c may be selected so that a+b+c may not exceed a valence of Ar.

The fullerene derivative according to an example embodiment may have a structure substituted with the substituent of Chemical Formula 1 having a fused ring structure of an X-containing pentagonal ring and an aromatic ring and thus increase steric hindrance but decrease a pi (π)-conjugation structure compared with unsubstituted fullerene. Accordingly, the fullerene derivative may have a shallow LUMO energy level and low bandgap energy compared with those of the unsubstituted fullerene and thus high electron acceptability and absorb light of a long wavelength region.

A LUMO energy level of the fullerene derivative may be about 2.6 eV to about 4.1 eV, for example about 2.6 eV to about 4.0 eV, about 2.6 eV to about 3.9 eV, or about 2.6 eV to about 3.8 eV and a HOMO energy level may be about 5.5 eV to about 6.9 eV, for example about 5.5 eV to about 6.8 eV, about 5.5 eV to about 6.7 eV, or about 5.5 eV to about 6.6 eV. In addition, the fullerene derivative may have a bandgap energy of greater than or equal to about 2.46 eV, for example greater than or equal to about 2.47 eV, or greater than or equal to about 2.48 eV and less than or equal to about 2.56 eV, for example less than or equal to about 2.55 eV, or less than or equal to about 2.54 eV.

The fullerene derivative may be effectively used as an n-type semiconductor by having the energy levels and low bandgap energy within the ranges, extending an absorption wavelength of light (e.g. sunlight) to a longer wavelength region, and improving electron affinity for electrons and thus improving electron acceptability.

The fullerene derivative may have excellent electron acceptability and may exhibit reversible peaks in the current-voltage curve line of cyclic-voltammetry (CV). The fullerene derivative may exhibit three or more reduction peaks at about −1.0 V to about −2.0 V in the current-voltage curve line of cyclic-voltammetry. This reversible peak in the current-voltage curve line shows excellent electron acceptability. As such, the high electron acceptability may improve mobility by efficiently transporting charges while storing them in the compound.

In case that the electron acceptability effect is improved, external quantum efficiency (EQE) of the device may be improved. This external quantum efficiency is one of the values representing the efficiency of photoelectric conversion device, for example a semiconductor laser, a light emitting device such as a light emitting diode, and the like or a light receiving device such as a photodiode (OPD) or a photodetector. If the fullerene derivative acting as an electron acceptor has good electron acceptability, recombination with holes may be also suppressed, increasing external quantum efficiency.

Such electron acceptability effects may be obtained when X is S in the X-containing pentagonal ring, and such effects may not be obtained when X is O or N.

In addition, when the fullerene derivative including the substituent represented by Chemical Formula 1 is deposited, aggregation may be reduced and thus film-formation characteristics may be improved, and transformation of optical properties due to the aggregation may be reduced. When the fullerene derivative has the substituent represented by Chemical Formula 1, a sublimation temperature may be decreased, and accordingly, the fullerene derivative may be vacuum-deposited without decomposition, for example, vacuum-deposited by sublimation with high purity. This effect may be further improved, when $R^1$ to $R^3$ of Chemical Formula 1 have a bulky substituent (e.g., a branched substituent and the like).

Vacuum-deposition by sublimation may be confirmed by a thermogravimetric analysis (TGA), and during a thermogravimetric analysis at a pressure of less than or equal to about 0.1 Pa, a temperature at which a weight loss of 10 wt % relative to an initial weight occurs may be less than or equal to about 450° C., and a temperature at which a weight loss of 50 wt % relative to an initial weight occurs may be may be less than or equal to about 500° C.

For example, the fullerene derivative may exhibit a weight loss of 10 wt % relative to an initial weight at about 300° C. to about 450° C. and a weight loss of 50 wt % relative to an initial weight at about 380° C. to about 500° C., during a thermogravimetric analysis at a pressure of less than or equal to about 0.1 Pa. For example, a weight loss of 10 wt % relative to an initial weight may occur at about 310° C. to about 445° C. and a weight loss of 50 wt % relative to an initial weight may occur at about 420° C. to about 490° C., for example a weight loss of 10 wt % relative to an initial weight may occur at about 310° C. to about 425° C. and a weight loss of 50 wt % relative to an initial weight may occur at about 420° C. to about 470° C., for example a weight loss of 10 wt % relative to an initial weight may occur about 310° C. to about 410° C. and a weight loss of 50 wt % relative to an initial weight may occur about 420° C. to about 460° C.

In an embodiment, the fullerene derivative including the fullerene core combined with the substituent represented by Chemical Formula 1 may be represented by Chemical Formula 1A.

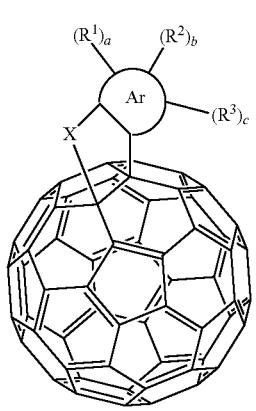

[Chemical Formula 1A]

In Chemical Formula 1A,

X, Ar, $R^1$ to $R^3$, a, b, and c are the same as in Chemical Formula 1.

In Chemical Formula 1, Ar may be a benzene ring or a fused ring. In an embodiment, Ar may be a benzene ring, a naphthalene ring, an anthracene ring, a phenanthrene ring, a pyrene ring, or a triphenylene ring. In an embodiment, Ar may be a benzene ring or a naphthalene ring.

In an embodiment, at least one, for example at least two or three of $R^1$ to $R^3$ of Chemical Formula 1 may be a linear substituent selected from a substituted or unsubstituted C1 to C20 linear alkyl group, for example a substituted or unsubstituted C4 to C20 linear alkyl group or a substituted or unsubstituted C5 to C15 linear alkyl group; a substituted or unsubstituted C2 to C20 linear alkenyl group, for example a substituted or unsubstituted C4 to C20 linear alkenyl group or a substituted or unsubstituted C5 to C15 linear alkenyl group; a substituted or unsubstituted C2 to C20 linear alkynyl group, for example a substituted or unsubstituted C4 to C20 linear alkynyl group or a substituted or unsubstituted C5 to C15 linear alkynyl group; a substituted or unsubstituted C1 to C20 linear heteroalkyl group, for example a substituted or unsubstituted C4 to C20 linear heteroalkyl group or a substituted or unsubstituted C5 to C15 linear heteroalkyl group; a substituted or unsubstituted C2 to C20 linear heteroalkenyl group, for example a substituted or unsubstituted C4 to C20 linear heteroalkenyl group or a substituted or unsubstituted C5 to C15 linear heteroalkenyl group; a substituted or unsubstituted C2 to C20 linear heteroalkynyl group, for example a substituted or unsubstituted C4 to C20 linear heteroalkynyl group, or a substituted or unsubstituted C5 to C15 linear heteroalkynyl group; or a combination thereof.

In an embodiment, at least one, for example at least two or three of $R^1$ to $R^3$ of Chemical Formula 1 may be a branched substituent selected from a substituted or unsubstituted C3 to C20 branched alkyl group, for example a substituted or unsubstituted C4 to C20 branched alkyl group or a substituted or unsubstituted C5 to C15 branched alkyl group; a substituted or unsubstituted C3 to C20 branched alkenyl group, for example a substituted or unsubstituted C4 to C20 branched alkenyl group or a substituted or unsubstituted C5 to C15 branched alkenyl group; a substituted or unsubstituted C3 to C20 branched alkynyl group, for example a substituted or unsubstituted C4 to C20 branched alkynyl group or a substituted or unsubstituted C5 to C15 branched alkynyl group; a substituted or unsubstituted C3 to C20 branched heteroalkyl group, for example a substituted or unsubstituted C4 to C20 branched heteroalkyl group or a substituted or unsubstituted C5 to C15 branched heteroalkyl group; a substituted or unsubstituted C3 to C20 branched heteroalkenyl group, for example a substituted or unsubstituted C4 to C20 branched heteroalkenyl group or a substituted or unsubstituted C5 to C15 branched heteroalkenyl group; a substituted or unsubstituted C3 to C20 branched heteroalkynyl group, for example a substituted or unsubstituted C4 to C20 branched heteroalkynyl group or a substituted or unsubstituted C5 to C15 branched heteroalkynyl group; or a combination thereof.

In an embodiment, at least one, for example at least two or three of $R^1$ to $R^3$ of Chemical Formula 1 may be a cyclic substituent selected from a substituted or unsubstituted C6 to C30 aryl group, for example a substituted or unsubstituted C6 to C20 aryl group, a substituted or unsubstituted C3 to C30 cycloalkyl group, for example a substituted or unsubstituted C3 to C20 cycloalkyl group, a substituted or unsubstituted C3 to C30 heterocyclic group, for example a substituted or unsubstituted C3 to C20 heterocyclic group, or a combination thereof.

At least one of $R^1$ to $R^3$ may be the linear substituent, and at least one of $R^1$ to $R^3$ may be the branched substituent or the cyclic substituent. For example, two of $R^1$ to $R^3$ may be the linear substituent and the other one of $R^1$ to $R^3$ may be the branched substituent or the cyclic substituent. In addition, one of $R^1$ to $R^3$ may be the linear substituent and the other two of $R^1$ to $R^3$ may be the branched substituent or the cyclic substituent.

At least one of $R^1$ to $R^3$ may be the branched substituent and at least one of $R^1$ to $R^3$ may be the cyclic substituent.

In an embodiment, the substituted or unsubstituted C3 to C20 branched alkyl group, a substituted or unsubstituted C3 to C20 branched alkenyl group, or a substituted or unsubstituted C3 to C20 branched alkynyl group may be represented by Chemical Formula 1-1.

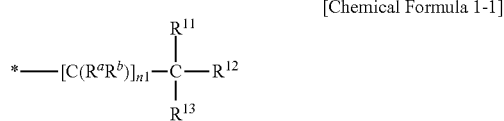

[Chemical Formula 1-1]

In Chemical Formula 1-1, $R^a$ and $R^b$ is hydrogen, a halogen, a cyano group, or a C1 to C6 alkyl group, n1 is an integer of 0 to 10, and $R^{11}$ to $R^{13}$ is hydrogen, a halogen, a cyano group, a C1 to C10 alkyl group, a C1 to C10 alkoxy group, a C2 to C10 alkenyl group, or a C2 to C10 alkynyl group, provided that at least two of $R^{11}$ to $R^{13}$ are a C1 to C10 alkyl group, a C1 to C10 alkoxy group, a C2 to C10 alkenyl group, or a C2 to C10 alkynyl group.

In some amendments, when the substituted or unsubstituted C3 to C20 branched alkyl group is represented by Chemical Formula 1-1, at least two of $R^{11}$ to $R^{13}$ are independently a C1 to C10 alkyl group;

when the substituted or unsubstituted C3 to C20 branched alkenyl group is represented by Chemical Formula 1-1, at least one of $R^{11}$ to $R^{13}$ is a C2 to C10 alkenyl group, and at least one of $R^{11}$ to $R^{13}$ is a C1 to C10 alkyl group; and when the substituted or unsubstituted C3 to C20 branched alkynyl group is represented by Chemical Formula 1-1, at least one of $R^{11}$ to $R^{13}$ is a C2 to C10 alkynyl group, and at least one of $R^{11}$ to $R^{13}$ is a C1 to C10 alkyl group.

In an embodiment, the C3 to C20 branched alkyl group may be an isopropyl group, an isobutyl group, an isopentyl group, an isohexyl group, a 2-ethylhexyl group, a 2-propylhexyl group, an isoheptyl group, a 2-ethylheptyl group, a 2-propylheptyl group, an isooctyl group, a 2-ethyloctyl group, a 2-propyloctyl group, a t-butyl group, a t-pentyl group, a t-hexyl group, a neopentyl group, or a neohexyl group, but is not limited thereto.

The C3 to C20 branched alkenyl group refers to a functional group including a double bond between carbons in the structure and the C3 to C20 branched alkynyl group refers to a functional group including triple bonds between carbons in the structure.

In addition, the C3 to C20 (branched) heteroalkyl group, the C3 to C20 (branched) heteroalkenyl group and the C3 to C20 (branched) heteroalkynyl group may include a (branched) alkyl group, a (branched) alkenyl group, and a (branched) alkynyl group in which a methylene group is replaced by —O—, —S—, —S(=O)—, —S(=O)$_2$—, —C(=O)—, —C(=O)O—, —OC(=O)—, or a combination thereof. For example, the C3 to C20 branched heteroalkyl group, C3 to C20 branched heteroalkenyl group, and C3 to C20 branched heteroalkynyl group may be a group obtain by replacing at least one —C($R^c R^d$)— in Chemical Formula 1-2 by a functional group selected from —O—, —S—, —S(=O)—, —S(=O)$_2$—, —C(=O)—, —C(=O)O—, —OC(=O)—, or a combination thereof.

[Chemical Formula 1-2]

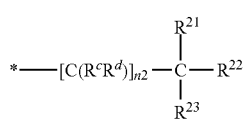

In Chemical Formula 1-2, $R^c$ and $R^d$ is hydrogen, a halogen, a cyano group, a C1 to C6 alkyl group, a C1 to C6 alkoxy group, a C2 to C10 ether group, or a C2 to C10 ester group, n2 is an integer of 2 to 10, and $R^{21}$ to $R^{23}$ is hydrogen, a halogen, a cyano group, a C1 to C10 alkyl group, a C1 to C10 alkoxy group, a C2 to C10 alkenyl group, or a C2 to C10 alkynyl group, provided that at least two of $R^{11}$ to $R^{13}$ are a C1 to C10 alkyl group, a C1 to C10 alkoxy group, a C2 to C10 alkenyl group, or a C2 to C10 alkynyl group.

In some amendments, in the case of the C3 to C20 branched heteroalkyl group, at least two of $R^{21}$ to $R^{23}$ are a C1 to C10 alkyl group;

in the case of the C3 to C20 branched heteroalkenyl group, at least one of $R^{21}$ to $R^{23}$ is a C2 to C10 alkenyl group, and at least one of $R^{21}$ to $R^{23}$ is a C1 to C10 alkyl group; and in the case of the C3 to C20 branched heteroalkynyl group, at least one of $R^{21}$ to $R^{23}$ is a C2 to C10 alkynyl group, and at least one of $R^{21}$ to $R^{23}$ is a C1 to C10 alkyl group.

The substituent represented by Chemical Formula 1 may be represented by one of Chemical Formulae 2A to 4A.

[Chemical Formula 2A]

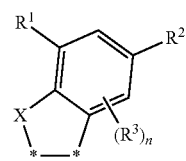

[Chemical Formula 2B]

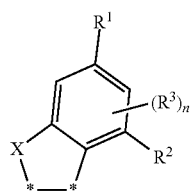

[Chemical Formula 3A]

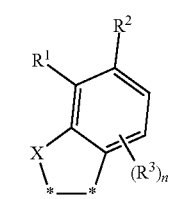

[Chemical Formula 3B]

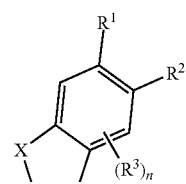

[Chemical Formula 3C]

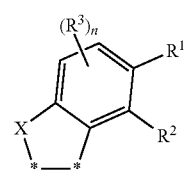

[Chemical Formula 4A]

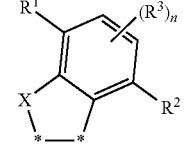

In Chemical Formulae 2A to 4A,

X is S, $R^1$ to $R^3$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, a substituted or unsubstituted C6 to C30 aryl group, a substituted or unsubstituted C3 to C30 cycloalkyl group, a substituted or unsubstituted C3 to C30 heterocyclic group, a halogen, a cyano group, or a combination thereof, n is an integer of 1 or 2, and

*—* is a linking portion with a fullerene core.

In an embodiment, at least one of $R^1$ and $R^2$, for example both $R^1$ and $R^2$ of Chemical Formulae 2A to 4A may be a linear substituent selected from a substituted or unsubstituted C1 to C20 linear alkyl group, for example a substituted or unsubstituted C4 to C20 linear alkyl group or a substituted or unsubstituted C5 to C15 linear alkyl group; a substituted or unsubstituted C2 to C20 linear alkenyl group, for example a substituted or unsubstituted C4 to C20 linear alkenyl group or a substituted or unsubstituted C5 to C15 linear alkenyl group; a substituted or unsubstituted C2 to C20 linear alkynyl group, for example a substituted or unsubstituted C4 to C20 linear alkynyl group or a substituted or unsubstituted C5 to C15 linear alkynyl group; a substituted or unsubstituted C1 to C20 linear heteroalkyl group, for example a substituted or unsubstituted C4 to C20 linear heteroalkyl group or a substituted or unsubstituted C5 to C15 linear heteroalkyl group; a substituted or unsubstituted C2 to C20 linear heteroalkenyl group, for example a substituted or unsubstituted C4 to C20 linear heteroalkenyl group or a substituted or unsubstituted C5 to C15 linear heteroalkenyl group; a substituted or unsubstituted C2 to C20 linear heteroalkynyl group, for example a substituted or unsubstituted C4 to C20 linear heteroalkynyl group or a substituted or unsubstituted C5 to C15 linear heteroalkynyl group; or a combination thereof.

In an embodiment, at least one of $R^1$ and $R^2$, for example both $R^1$ and $R^2$ of Chemical Formulae 2A to 4A may be a branched substituent selected from a substituted or unsubstituted C3 to C20 branched alkyl group, for example a substituted or unsubstituted C4 to C20 branched alkyl group or a substituted or unsubstituted C5 to C15 branched alkyl group; a substituted or unsubstituted C3 to C20 branched alkenyl group, for example a substituted or unsubstituted C4 to C20 branched alkenyl group or a substituted or unsubstituted C5 to C15 branched alkenyl group; a substituted or unsubstituted C3 to C20 branched alkynyl group, for example a substituted or unsubstituted C4 to C20 branched alkynyl group or a substituted or unsubstituted C5 to C15 branched alkynyl group; a substituted or unsubstituted C3 to C20 branched heteroalkyl group, for example a substituted or unsubstituted C4 to C20 branched heteroalkyl group or a substituted or unsubstituted C5 to C15 branched heteroalkyl group; a substituted or unsubstituted C3 to C20 branched heteroalkenyl group, for example a substituted or unsubstituted C4 to C20 branched heteroalkenyl group or a substituted or unsubstituted C5 to C15 branched heteroalkenyl group; a substituted or unsubstituted C3 to C20 branched heteroalkynyl group, for example a substituted or unsubstituted C4 to C20 branched heteroalkynyl group or a substituted or unsubstituted C5 to C15 branched heteroalkynyl group; or a combination thereof.

In an embodiment, at least one of $R^1$ and $R^2$, for example both $R^1$ and $R^2$ of Chemical Formulae 2A to 4A may be a cyclic substituent selected from a substituted or unsubstituted C6 to C30 aryl group, for example a substituted or unsubstituted C6 to C20 aryl group, a substituted or unsubstituted C3 to C30 cycloalkyl group, for example a substituted or unsubstituted C3 to C20 cycloalkyl group, a substituted or unsubstituted C3 to C30 heterocyclic group, for example a substituted or unsubstituted C3 to C20 heterocyclic group, or a combination thereof.

In Chemical Formulae 2A to 4A, one of $R^1$ and $R^2$ may be the linear substituent and the other of $R^1$ and $R^2$ may be the branched substituent or the cyclic substituent.

In Chemical Formulae 2A to 4A, one of $R^1$ and $R^2$ may be the branched substituent and the other of $R^1$ and $R^2$ may be the cyclic substituent.

The substituent represented by Chemical Formula 1 may be represented by one of Chemical Formulae 5A to 7B.

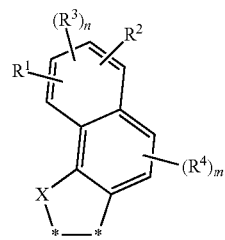

[Chemical Formula 5A]

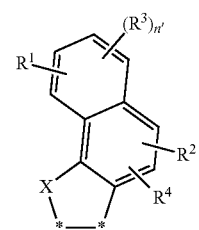

[Chemical Formula 5B]

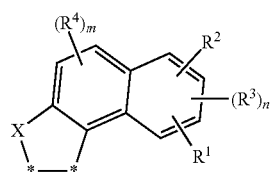

[Chemical Formula 6A]

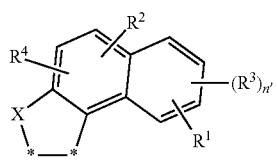

[Chemical Formula 6B]

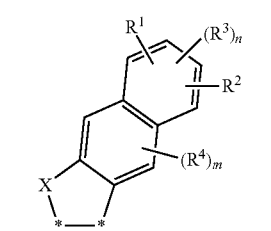

[Chemical Formula 7A]

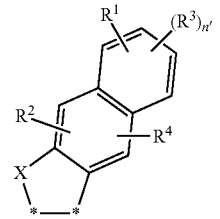

[Chemical Formula 7B]

In Chemical Formulae 5A to 7B,
X is S,
$R^1$ to $R^4$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, a substituted or unsubstituted C6 to C30 aryl group, a substituted or unsubstituted C3 to C30 cycloalkyl group, a substituted or unsubstituted C3 to C30 heterocyclic group, a halogen, a cyano group, or a combination thereof, n and m are independently an integer of 1 or 2, n' is an integer of 1 to 3, and

*—* is a linking portion with a fullerene core.

In an embodiment, at least one of $R^1$ and $R^2$, for example both $R^1$ and $R^2$ of Chemical Formulae 5A to 7B may be a linear substituent selected from a substituted or unsubstituted C1 to C20 linear alkyl group, for example a substituted or unsubstituted C4 to C20 linear alkyl group or a substituted or unsubstituted C5 to C15 linear alkyl group; a substituted or unsubstituted C2 to C20 linear alkenyl group, for example a substituted or unsubstituted C4 to C20 linear alkenyl group or a substituted or unsubstituted C5 to C15 linear alkenyl group; a substituted or unsubstituted C2 to C20 linear alkynyl group, for example a substituted or unsubstituted C4 to C20 linear alkynyl group or a substituted or unsubstituted C5 to C15 linear alkynyl group; a substituted or unsubstituted C1 to C20 linear heteroalkyl group, for example a substituted or unsubstituted C4 to C20 linear heteroalkyl group or a substituted or unsubstituted C5 to C15 linear heteroalkyl group; a substituted or unsubstituted C2 to C20 linear heteroalkenyl group, for example a substituted or unsubstituted C4 to C20 linear heteroalkenyl group or a substituted or unsubstituted C5 to C15 linear heteroalkenyl group; a substituted or unsubstituted C2 to C20 linear heteroalkynyl group, for example a substituted or unsubstituted C4 to C20 linear heteroalkynyl group or a substituted or unsubstituted C5 to C15 linear heteroalkynyl group; or a combination thereof.

In an embodiment, at least one of $R^1$ and $R^2$, for example both $R^1$ and $R^2$ of Chemical Formulae 5A to 7B may be branched substituent selected from a substituted or unsubstituted C3 to C20 branched alkyl group, for example a substituted or unsubstituted C4 to C20 branched alkyl group or a substituted or unsubstituted C5 to C15 branched alkyl group; a substituted or unsubstituted C3 to C20 branched alkenyl group, for example a substituted or unsubstituted C4 to C20 branched alkenyl group or a substituted or unsubstituted C5 to C15 branched alkenyl group; a substituted or unsubstituted C3 to C20 branched alkynyl group, for example a substituted or unsubstituted C4 to C20 branched alkynyl group or a substituted or unsubstituted C5 to C15 branched alkynyl group; a substituted or unsubstituted C3 to C20 branched heteroalkyl group, for example a substituted or unsubstituted C4 to C20 branched heteroalkyl group or a substituted or unsubstituted C5 to C15 branched heteroalkyl group; a substituted or unsubstituted C3 to C20 branched heteroalkenyl group, for example a substituted or unsubstituted C4 to C20 branched heteroalkenyl group or a substituted or unsubstituted C5 to C15 branched heteroalkenyl group; a substituted or unsubstituted C3 to C20 branched heteroalkynyl group, for example a substituted or unsubstituted C4 to C20 branched heteroalkynyl group or a substituted or unsubstituted C5 to C15 branched heteroalkynyl group; or a combination thereof.

In an embodiment, at least one of $R^1$ and $R^2$, for example both $R^1$ and $R^2$ of Chemical Formulae 5A to 7B may be cyclic substituent selected from a substituted or unsubstituted C6 to C30 aryl group, for example a substituted or unsubstituted C6 to C20 aryl group, a substituted or unsubstituted C3 to C30 cycloalkyl group, for example a substituted or unsubstituted C3 to C20 cycloalkyl group, a substituted or unsubstituted C3 to C30 heterocyclic group, for example a substituted or unsubstituted C3 to C20 heterocyclic group, or a combination thereof.

In Chemical Formulae 5A to 7B, one of $R^1$ and $R^2$ may be a linear substituent and the other of $R^1$ and $R^2$ may be the branched substituent or the cyclic substituent.

In Chemical Formulae 5A to 7B, one of $R^1$ and $R^2$ may be the branched substituent and the other of $R^1$ and $R^2$ may be the cyclic substituent.

Specific examples of the fullerene derivatives include the following compounds.

[Group 1]

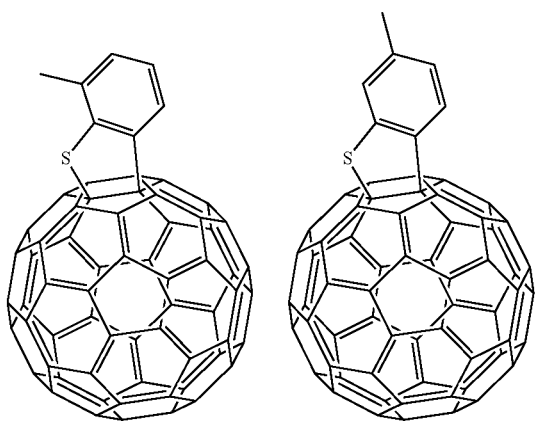

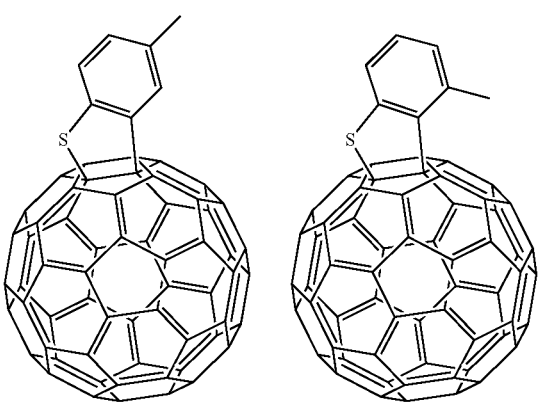

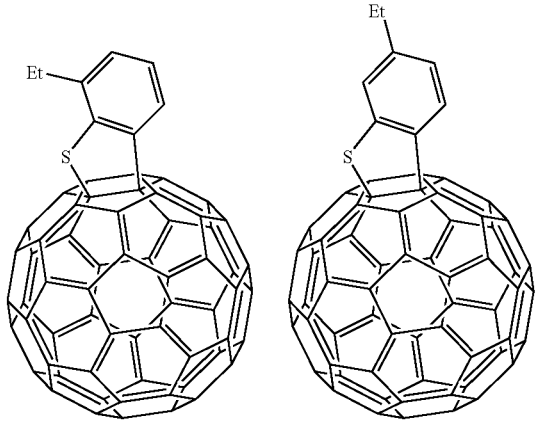

-continued
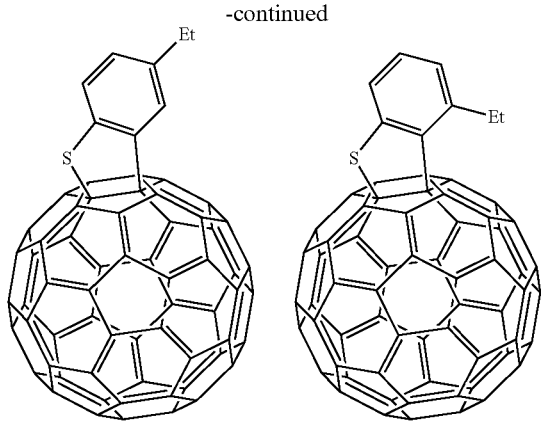
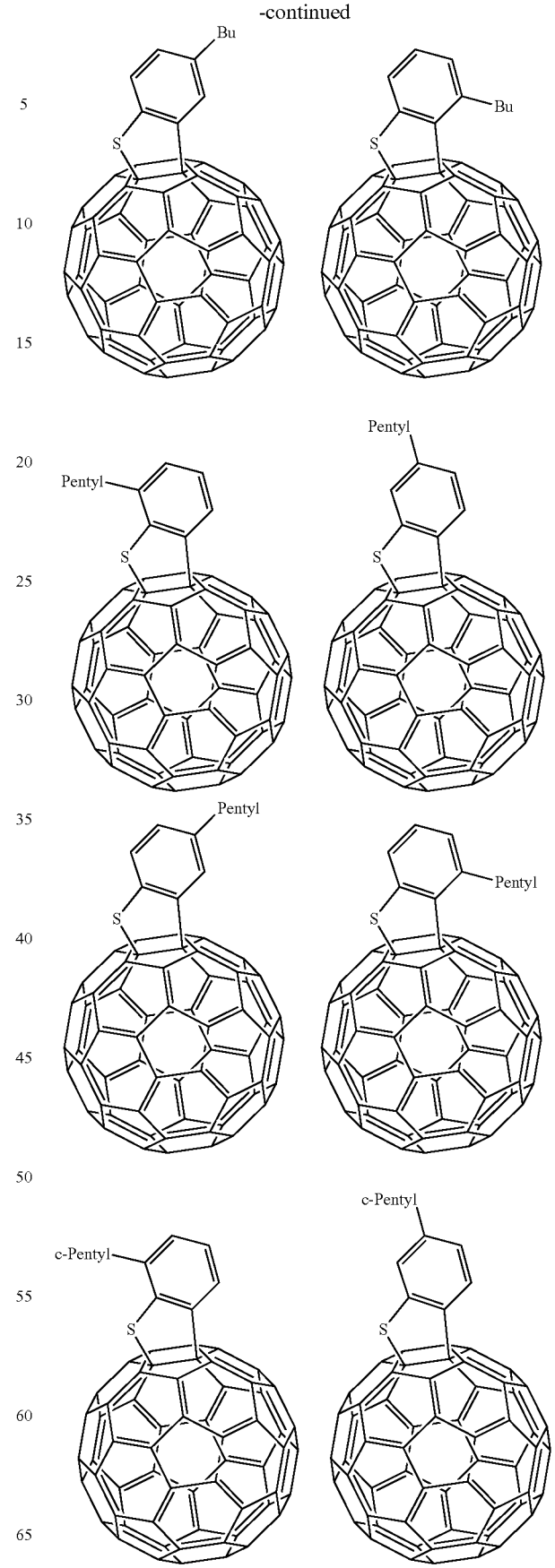

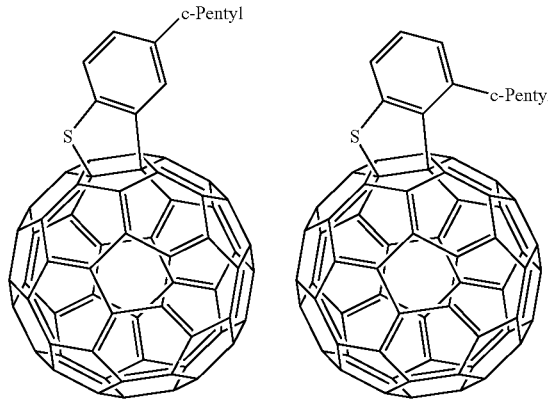
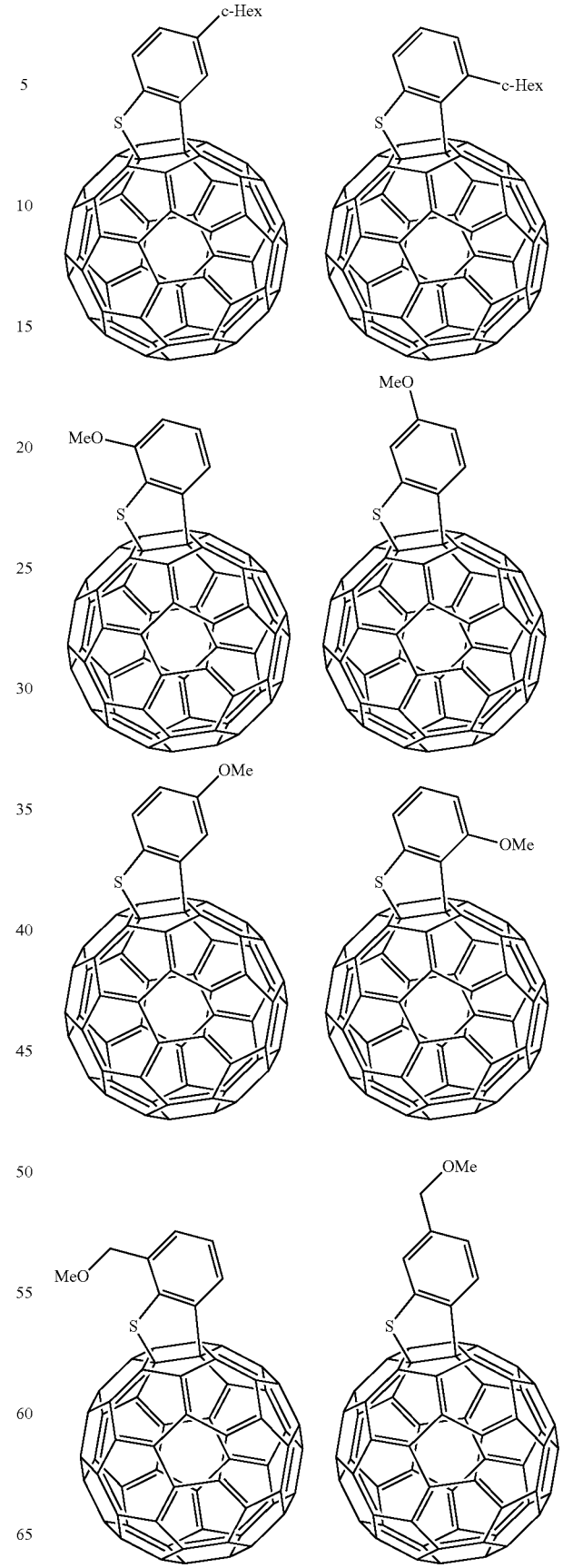

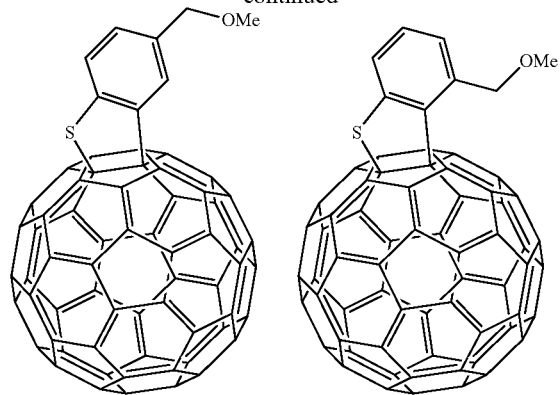
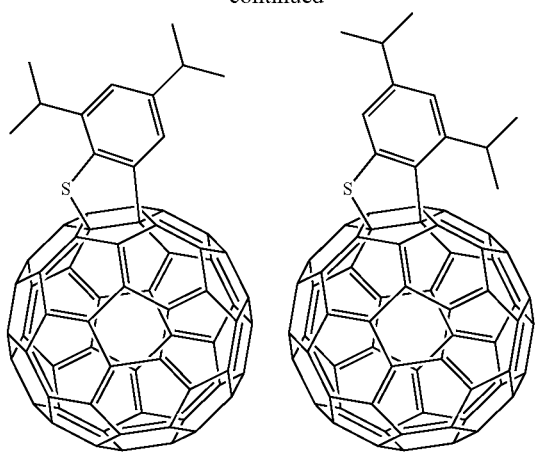
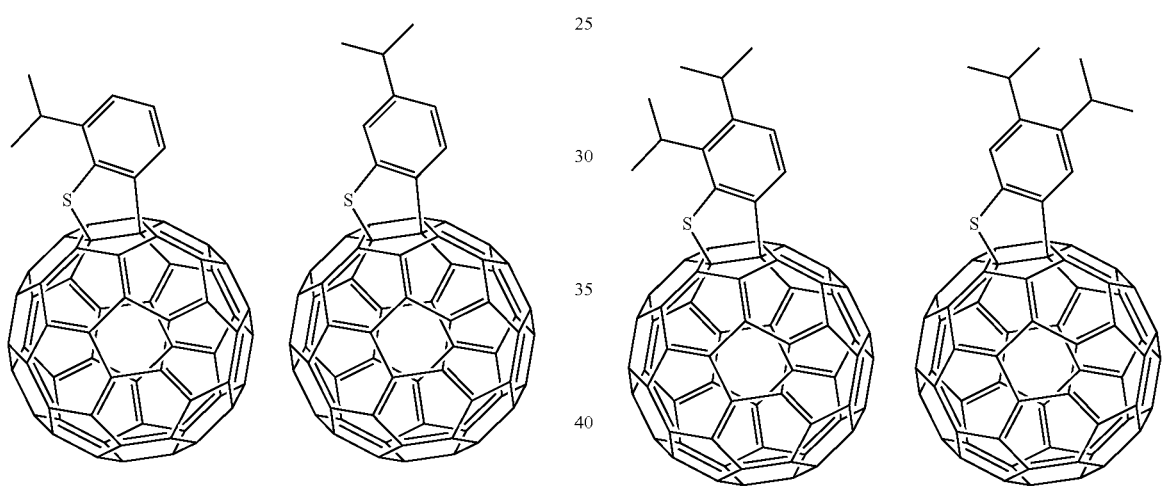
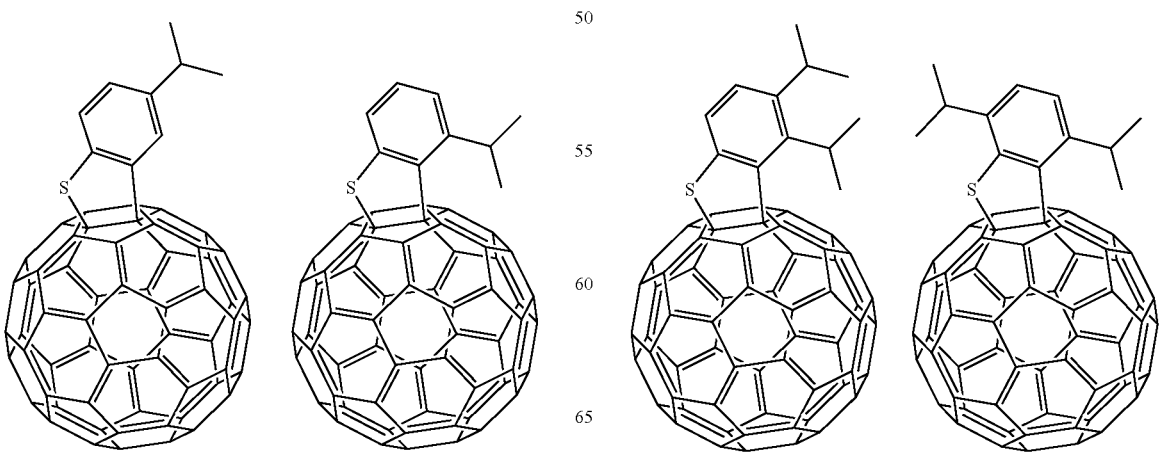

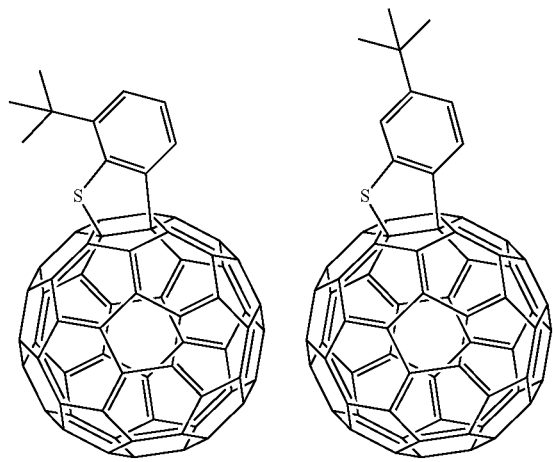
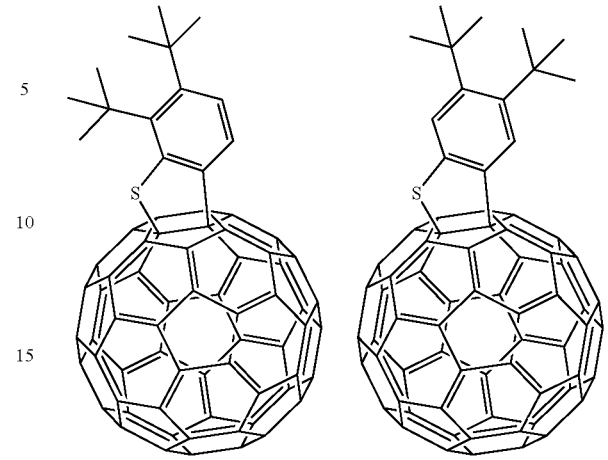
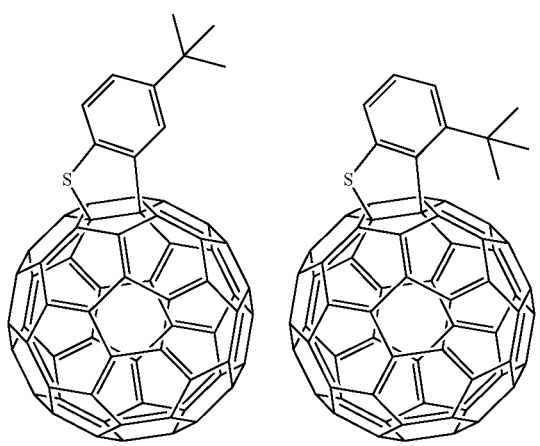
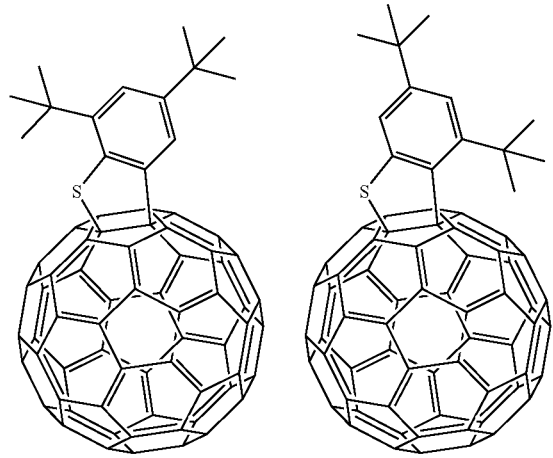

-continued
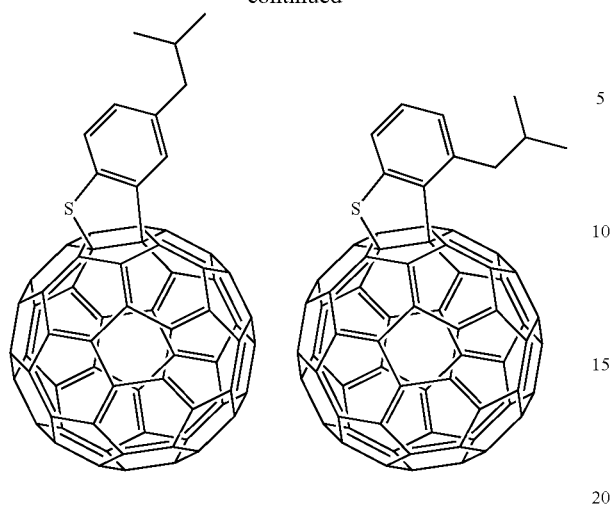
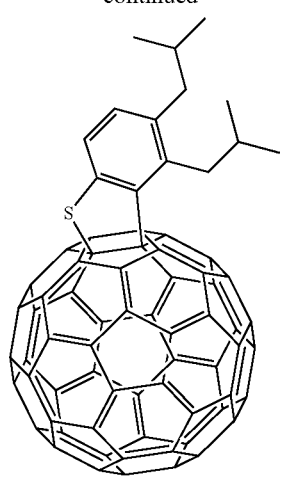
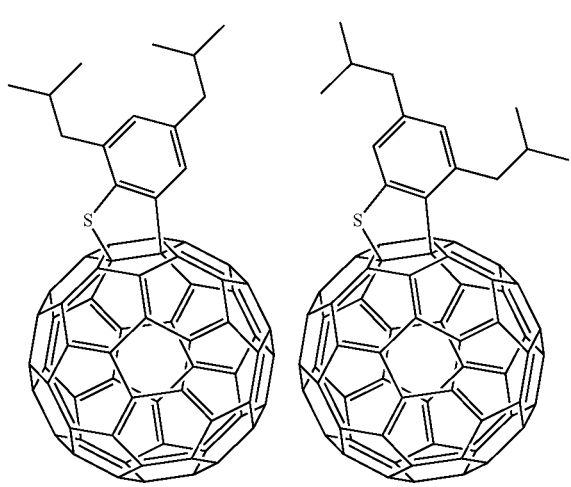
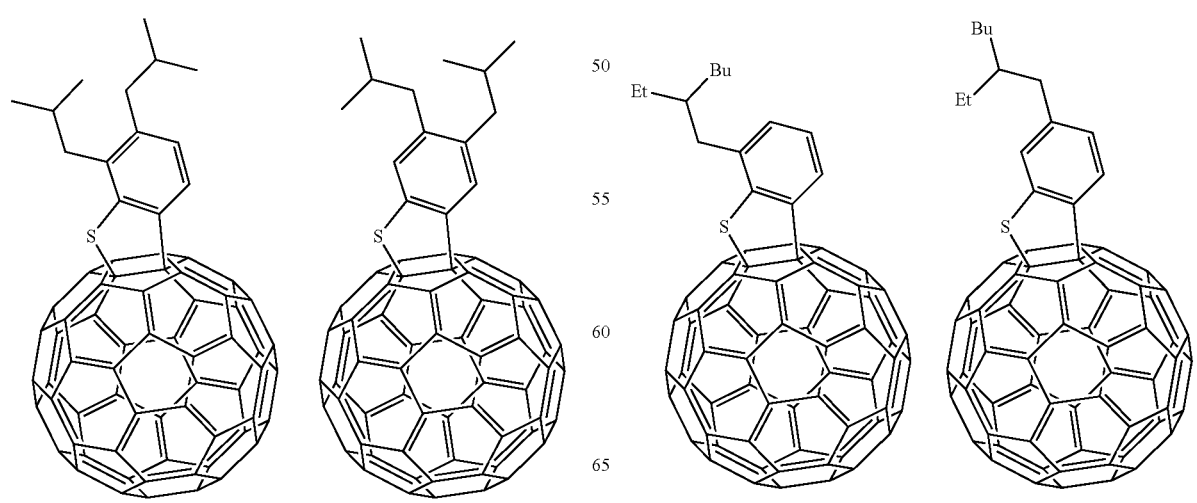

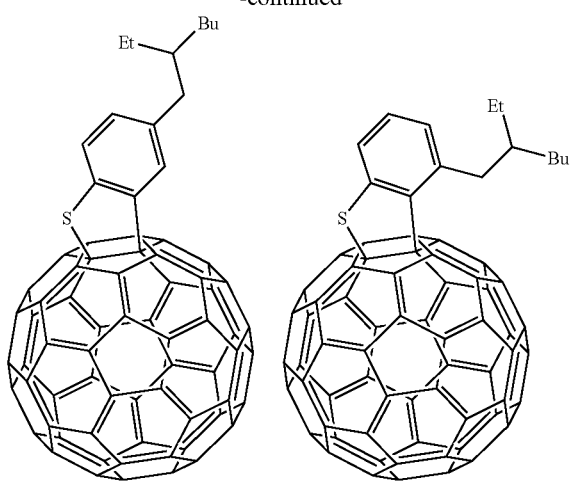
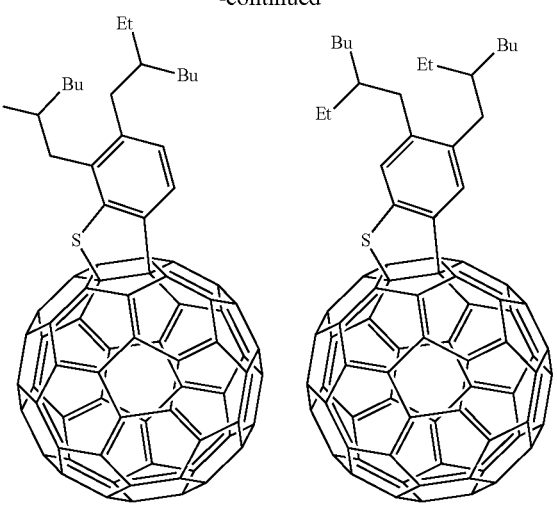
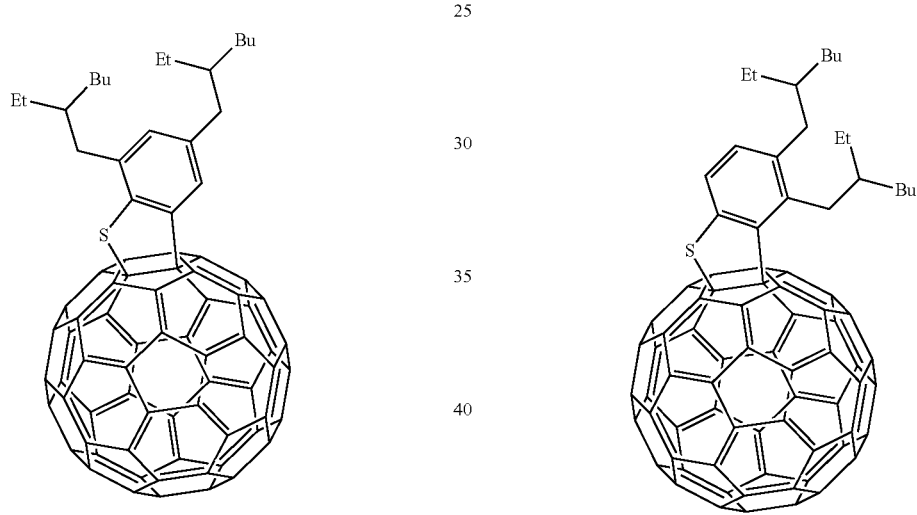
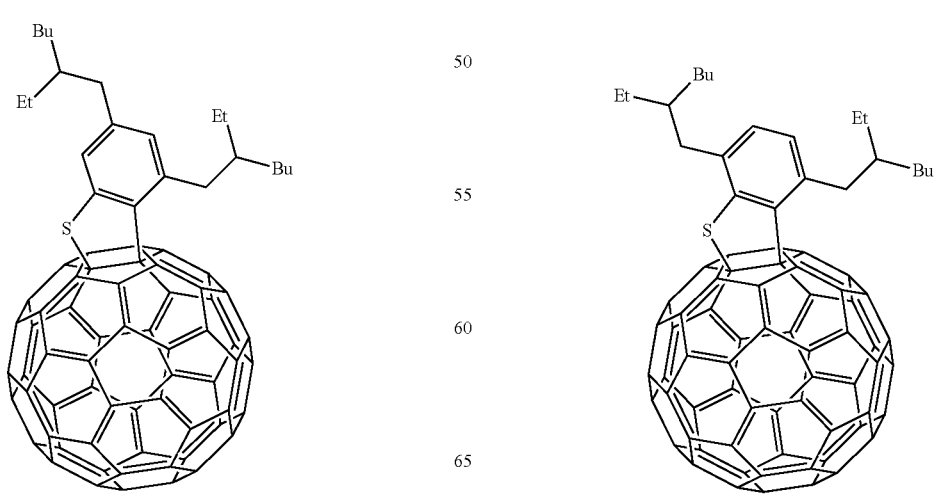

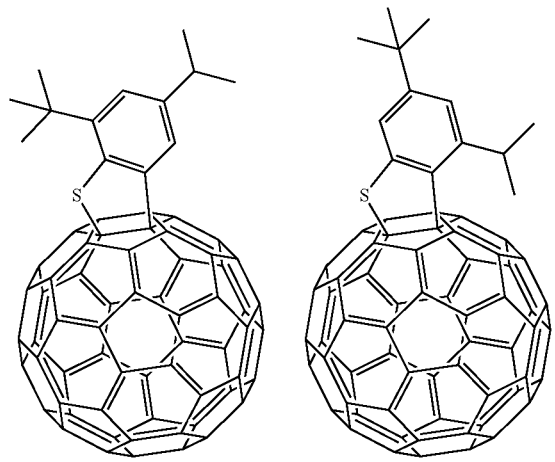
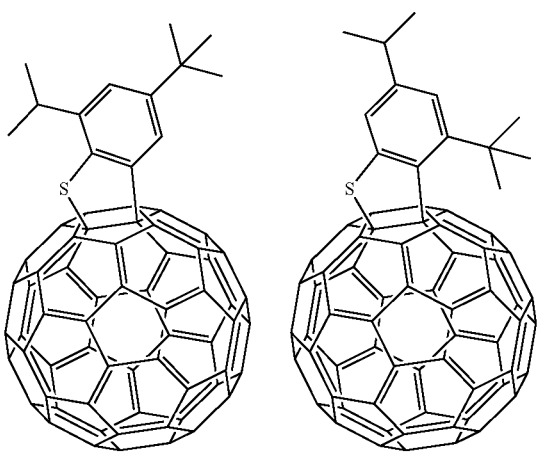
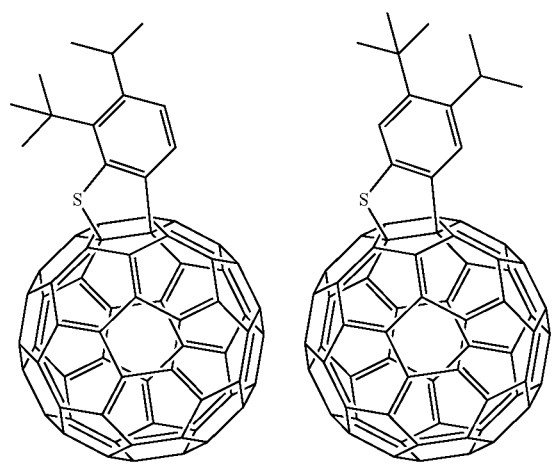
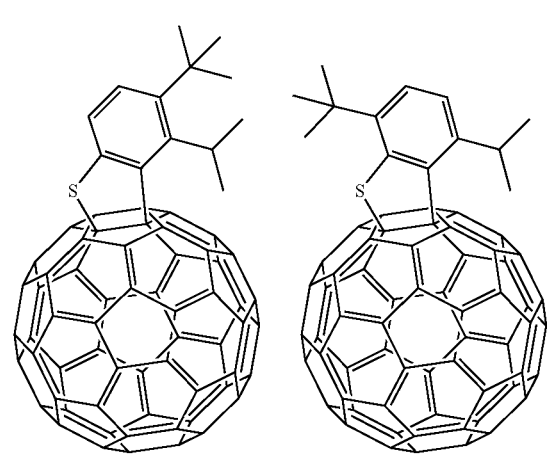

33
-continued
34
-continued
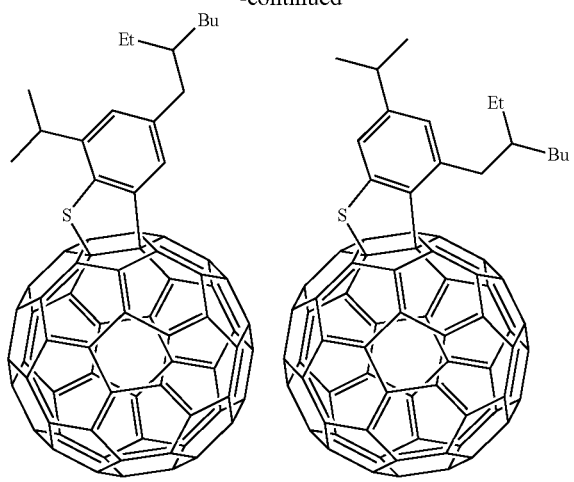
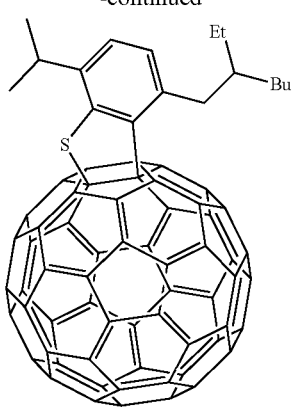
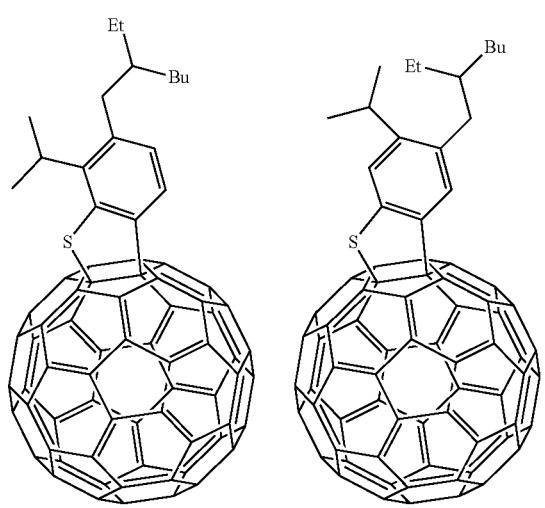
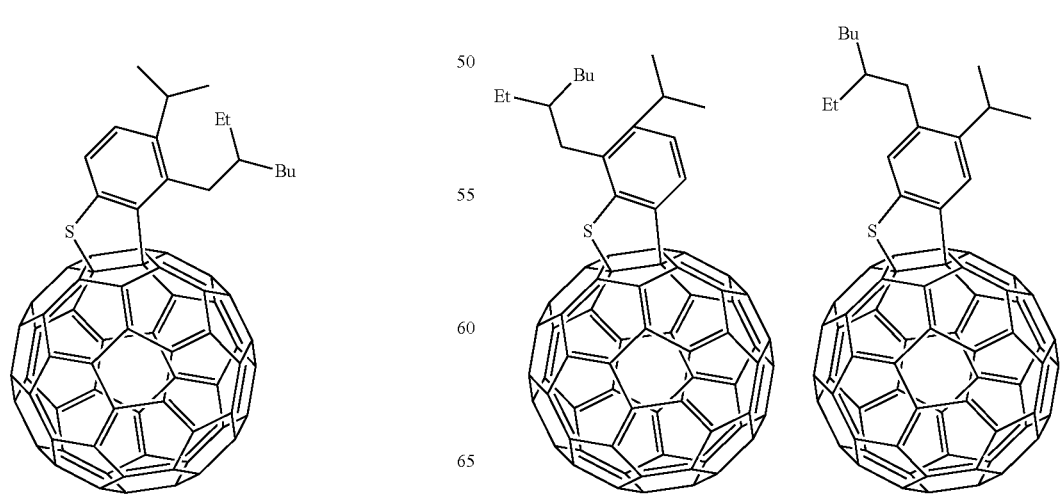

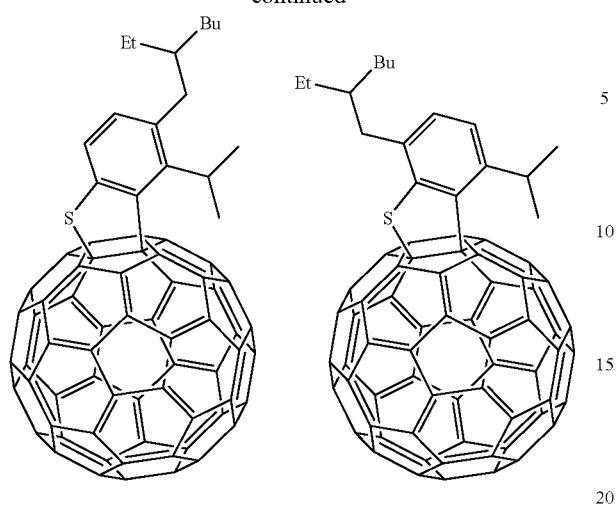
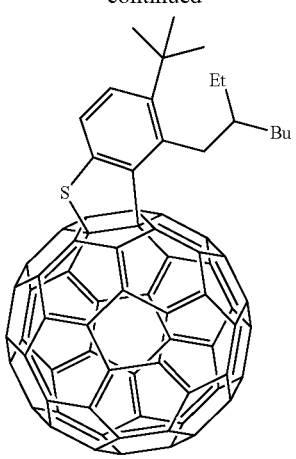
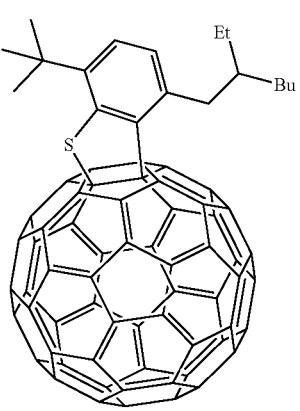
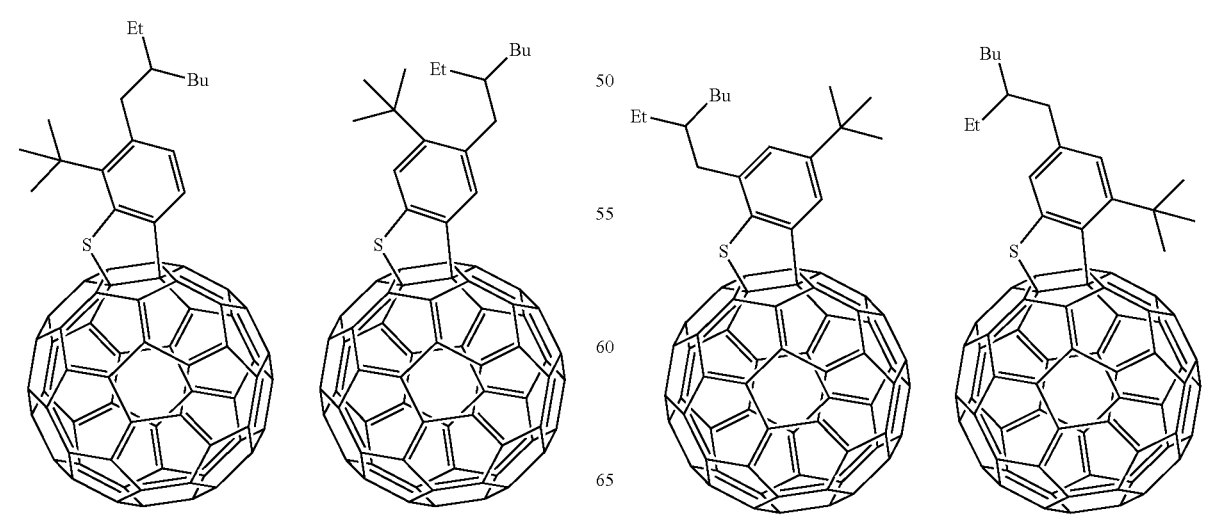

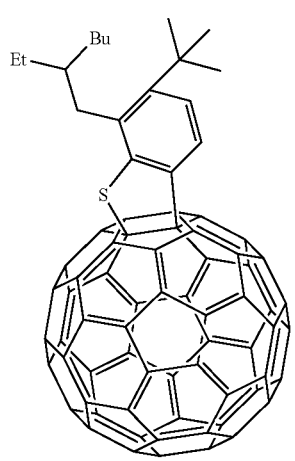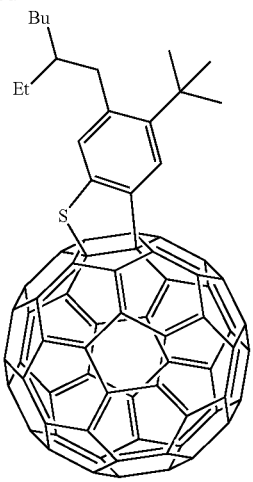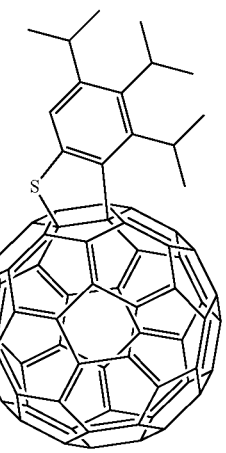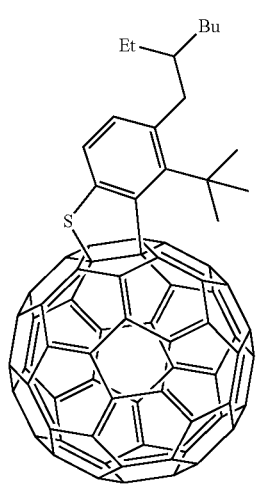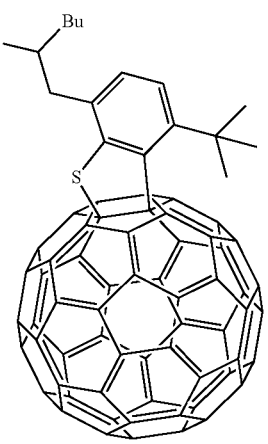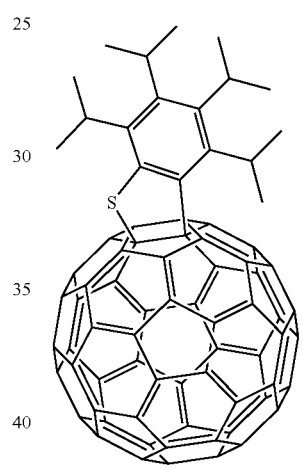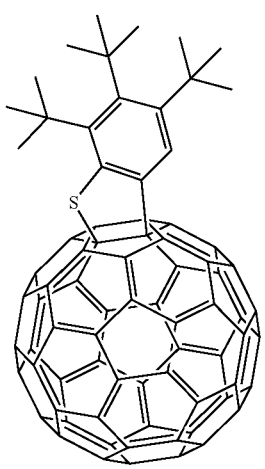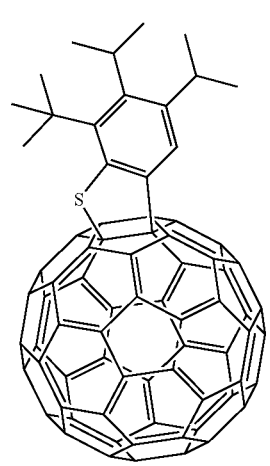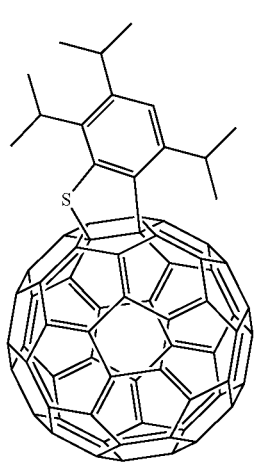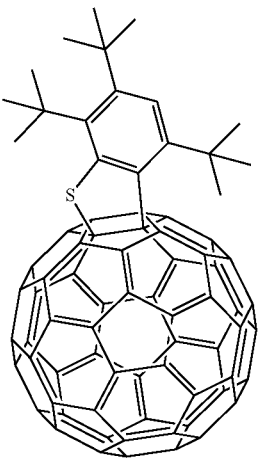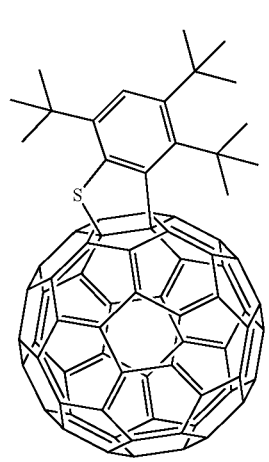

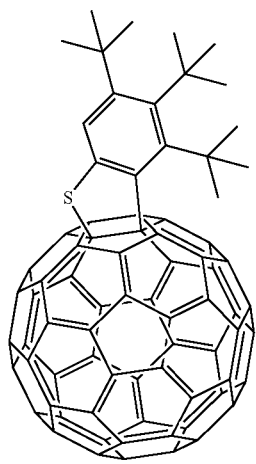 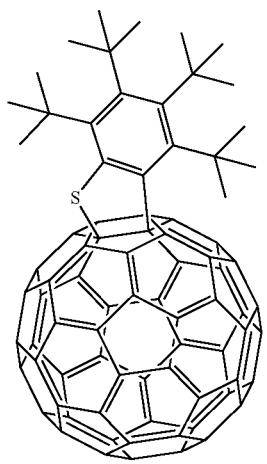 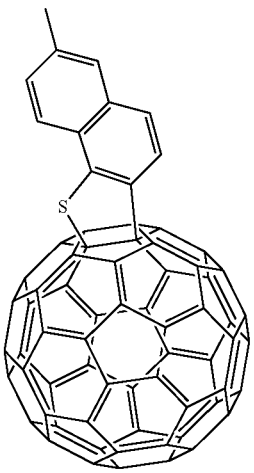 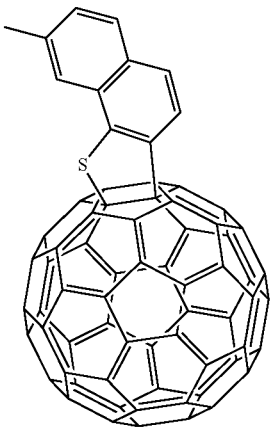
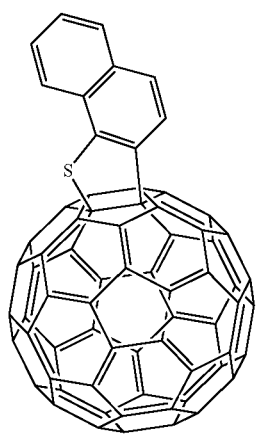 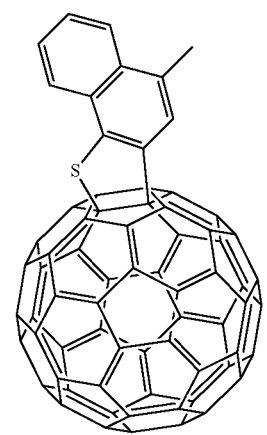 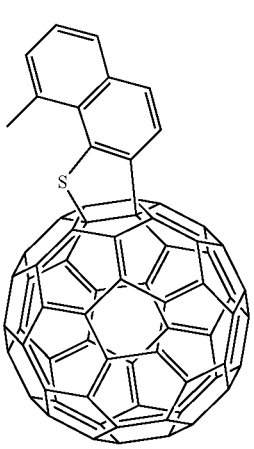 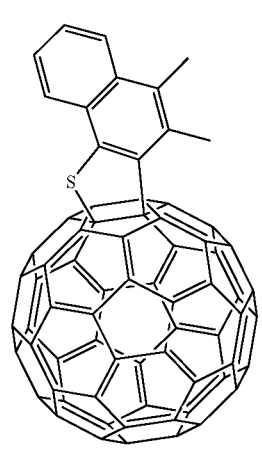
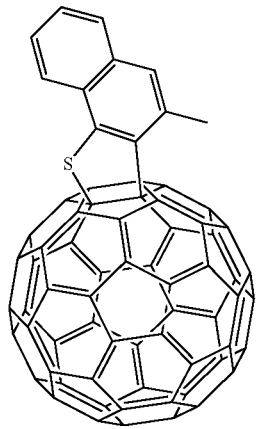 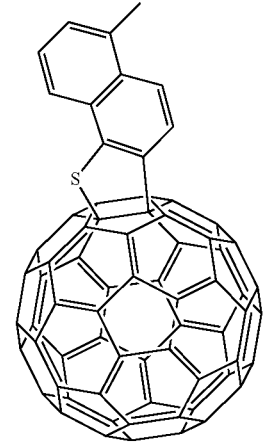 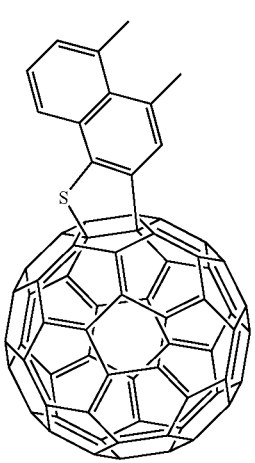 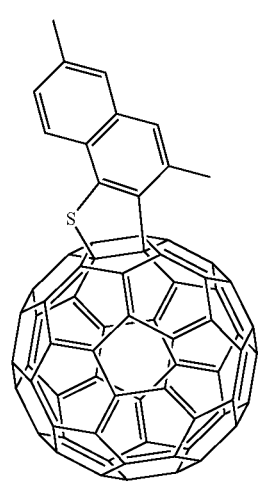

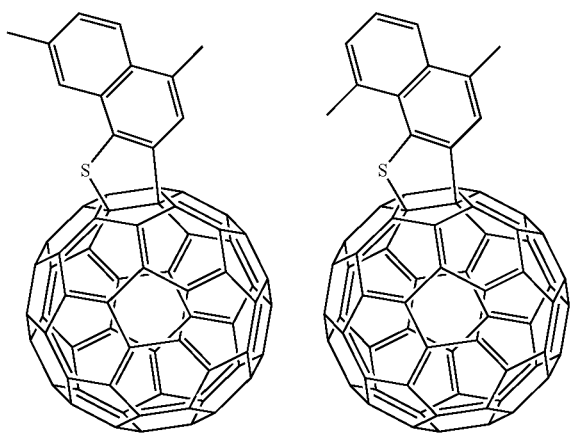
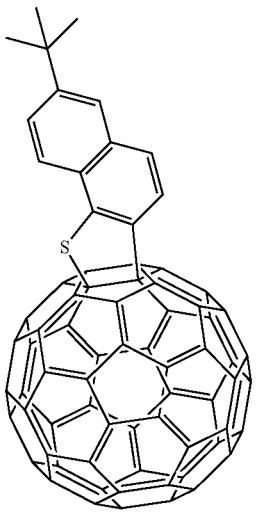
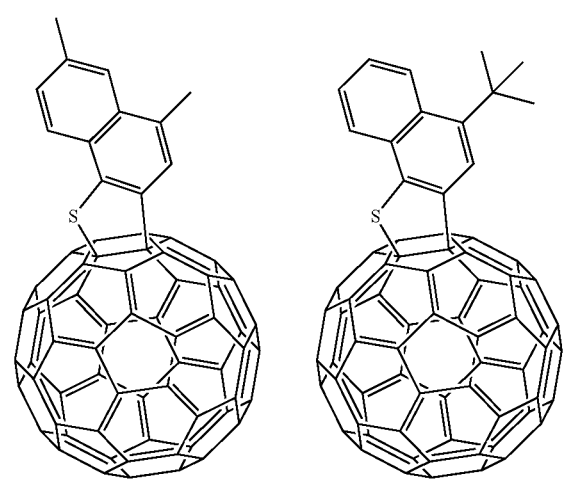
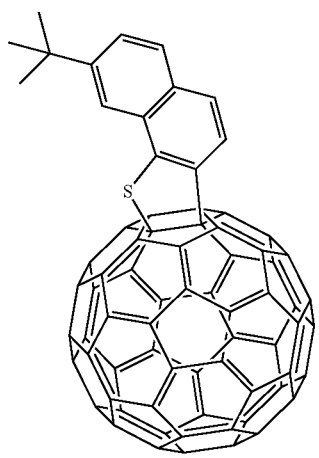
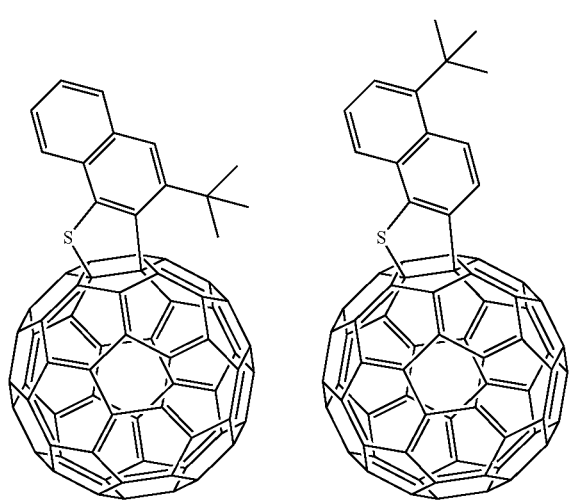
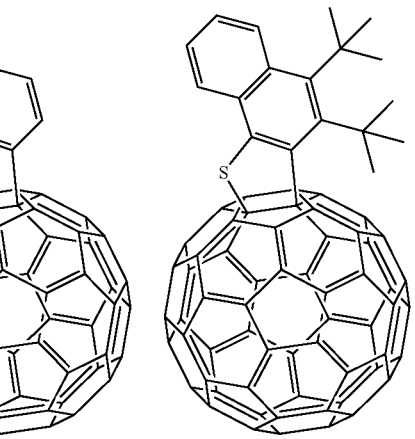

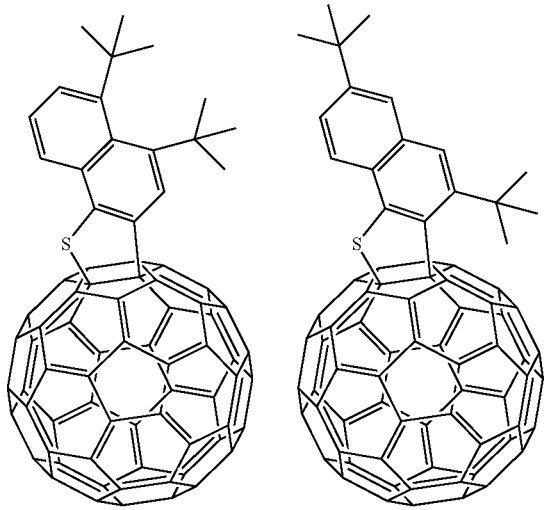

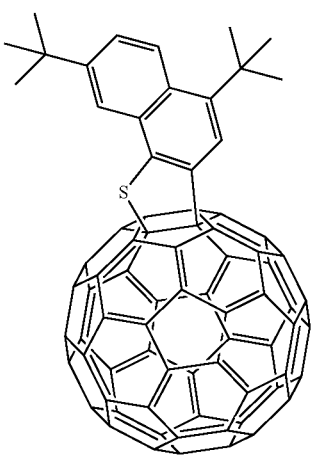

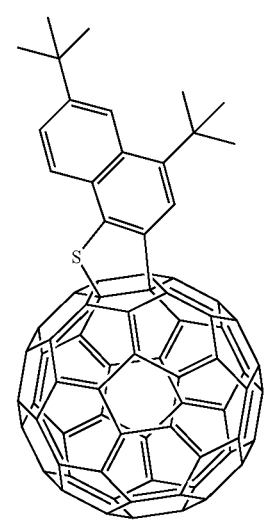

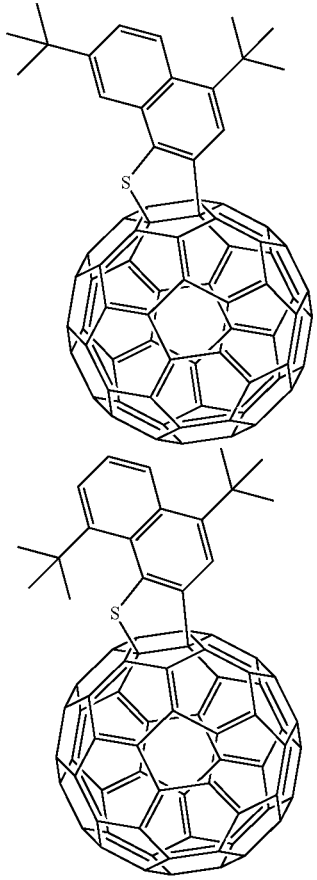

In Group 1, Et indicates ethyl, Pr indicates propyl, Bu indicates butyl, pentyl indicates pentyl, c-pentyl indicates cyclopentyl, Hex indicates hexyl, c-Hex indicates cyclohexyl, and OMe indicates methoxy.

In Group 1, at least one hydrogen of the aromatic ring may be further replaced by a C1 to C10 alkyl group, a C1 to C10 haloalkyl group, a halogen, and the like.

The fullerene core may be C60, C70, C74, C76, or C78. In an embodiment, the fullerene core may be C60.

The fullerene derivative may be prepared by reacting a substituent with the fullerene core, and may be synthesized with a high yield because it may be synthesized without going through a dimer unlike the manufacturing method of conventional fullerene derivative which forms an unstable dimer as an intermediate.

The fullerene derivative may be vacuum-deposited through sublimation into a thin film as described above. The thin film may maintain inherent characteristics of the fullerene derivative without breaking and/or transforming a chemical bond of the fullerene derivative, and accordingly, transformation of optical properties of the thin film may be reduced, compared with transformation of the optical properties due to an aggregation during deposition of a thin film including an unsubstituted fullerene (e.g., C60 fullerene). For example, the thin film including the fullerene derivative may have different light absorption characteristics from those of a thin film including unsubstituted fullerene (e.g., C60 fullerene), and for example, abnormal light absorption of the thin film including the fullerene derivative may be decreased in a short wavelength region of visible ray of about 400 nm to about 500 nm. For example, the thin film including the fullerene derivative may have a smaller absorption coefficient at a wavelength of 450 nm than that of the thin film including unsubstituted fullerene (e.g., C60 fullerene), for example, less than or equal to about ½ of the absorption coefficient of the thin film including unsubstituted fullerene (e.g., C60 fullerene).

Hereinafter, an organic photoelectric device including the aforementioned fullerene derivative is described.

FIG. 1 is a cross-sectional view showing an organic photoelectric device according to an embodiment.

Referring to FIG. 1, an organic photoelectric device 100 according to an embodiment includes a first electrode 10 and a second electrode 20 facing each other and an organic layer 30 disposed between the first electrode 10 and the second electrode 20.

A substrate (not shown) may be disposed on a surface of the first electrode 10 or a surface of the second electrode 20. The substrate may be for example made of an inorganic material such as glass, an organic material such as polycarbonate, polymethylmethacrylate, polyethyleneterephthalate, polyethylenenaphthalate, polyamide, polyethersulfone, or a combination thereof, or a silicon wafer. The substrate may be omitted.

One of the first electrode 10 and the second electrode 20 may be an anode and the other may be a cathode. For example, the first electrode 10 may be an anode and the second electrode 20 may be a cathode.

At least one of the first electrode 10 and the second electrode 20 may be a light-transmitting electrode and the light-transmitting electrode may be for example made of a conductive oxide such as an indium tin oxide (ITO), indium zinc oxide (IZO), zinc oxide (ZnO), tin oxide ($SnO_2$), aluminum tin oxide (AlTO), and fluorine doped tin oxide (FTO), or a metal thin layer of a single layer or a multilayer. When one of the first electrode 10 and the second electrode 20 is a non-light-transmitting electrode, it may be made of for example an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The organic layer 30 may include an active layer.

The active layer is a layer including a p-type semiconductor and an n-type semiconductor to provide a pn junction, which is a layer producing excitons by receiving light from outside and then separating holes and electrons from the produced excitons.

The p-type semiconductor and the n-type semiconductor may be light absorbing materials that absorb at least one part of each visible light region.

For example, the p-type semiconductor may be a light absorbing material that may mainly and selectively absorb one of light in a blue wavelength region of greater than or equal to about 400 nm and less than 500 nm, a green wavelength region of about 500 nm to about 600 nm, and a red wavelength region of greater than about 600 nm and less than or equal to about 700 nm, and the n-type semiconductor may be the aforementioned fullerene derivative. For example, the p-type semiconductor may be a light absorbing material that may mainly and selectively absorb light in a green wavelength region of about 500 nm to about 600 nm and the n-type semiconductor may be the aforementioned fullerene derivative.

For example, the p-type semiconductor may be for example a light absorbing material having a LUMO energy level of about 3.0 eV to about 3.6 eV and a HOMO energy level of about 5.1 eV to about 5.7 eV. Within the ranges, the p-type semiconductor may be for example a light absorbing material having a LUMO energy level of about 3.1 eV to about 3.5 eV and a HOMO energy level of about 5.2 eV to about 5.6 eV.

For example, the p-type semiconductor may be for example a light absorbing material having a core structure including an electron donating moiety, a pi conjugation linking group, and an electron accepting moiety.

The p-type semiconductor is a compound having the core structure and may include for example a compound represented by Chemical Formula 8, but is not limited thereto.

[Chemical Formula 8]

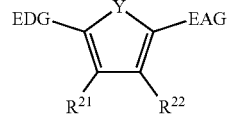

In Chemical Formula 8,
Y is Se, Te, S, SO, $SO_2$, or $SiR^hR^i$,
EDG is an electron donating group,
EAG is an electron accepting group, and
$R^{21}$, $R^{22}$, $R^h$, and $R^i$ are independently hydrogen or a monovalent substituent.

Herein, the monovalent substituent may be for example a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, but is not limited thereto.

The p-type semiconductor may be for example a light absorbing material represented by Chemical Formula 8A, but is not limited thereto.

[Chemical Formula 8A]

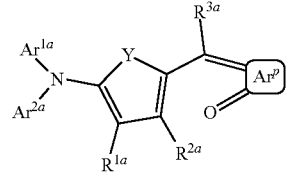

In Chemical Formula 8A,
Y is Se, Te, S, SO, $SO_2$, or $SiR^hR^i$,
$Ar^p$ is a substituted or unsubstituted 5-membered ring, a substituted or unsubstituted 6-membered ring, or a condensed ring of two or more of the foregoing rings,
$Ar^{1a}$ and $Ar^{2a}$ are independently a substituted or unsubstituted C6 to C30 aryl group or a substituted or unsubstituted C3 to C30 heteroaryl group, $Ar^{1a}$ and $Ar^{2a}$ are independently present or linked with each other by a linker of $G^1$ to form a ring, wherein $G^1$ is one of a single bond, —($CR^jR^k$)$_{n2}$—, —O—, —S—, —Se—, —N=, —NR'—, —$SiR^mR^n$—, and —$GeR^oR^p$— and n2 is 1 or 2, and
$R^{1a}$ to $R^{3a}$ and $R^h$ to $R^p$ are independently hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group.

The p-type semiconductor may be for example a light absorbing material represented by one of Chemical Formulae 8A-1 to 8A-4, but is not limited thereto.

[Chemical Formula 8A-1]

[Chemical Formula 8A-2]

[Chemical Formula 8A-3]

[Chemical Formula 8A-4]

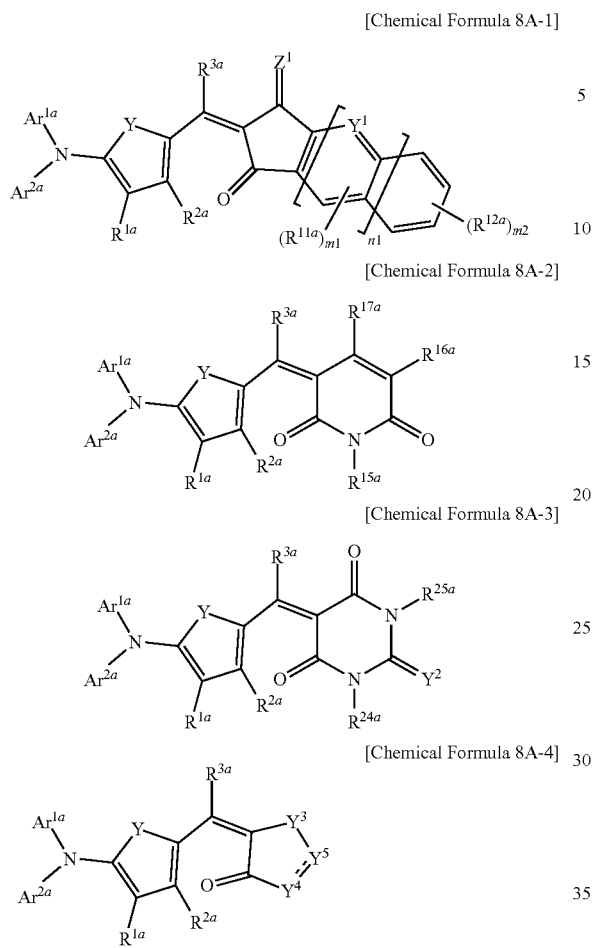

[Group 2]

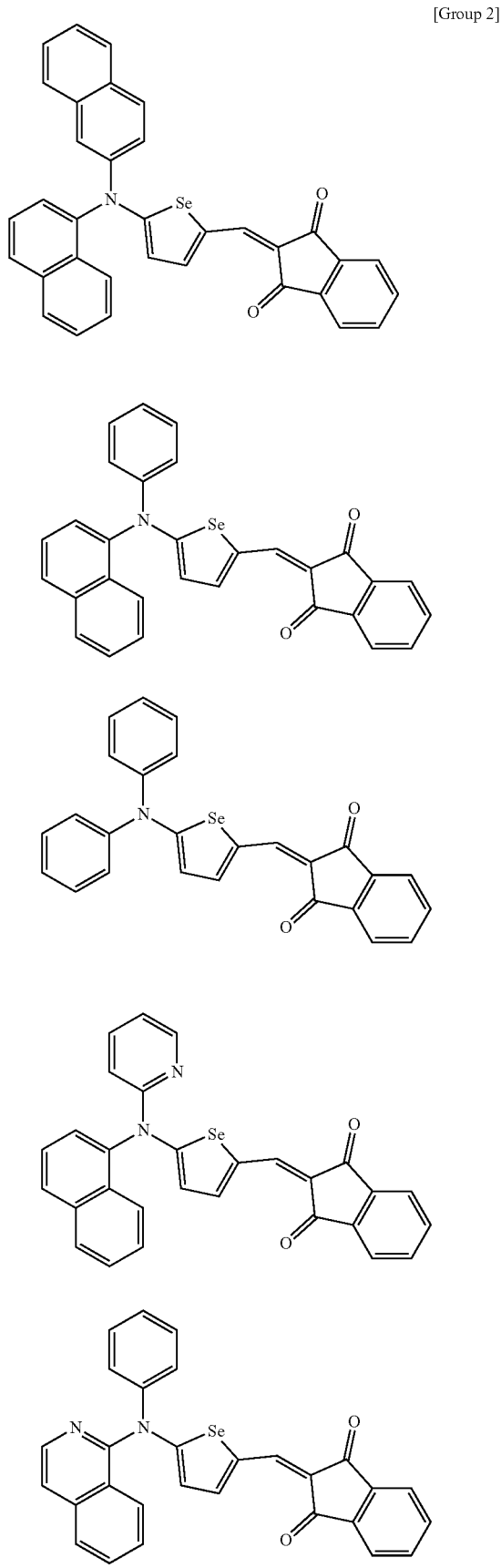

In Chemical Formulae 8A-1 to 8A-4,

Y is Se, Te, S, SO, $SO_2$, or $SiR^hR^i$, $Z^1$ is O or $CR^qR^r$, $Y^1$ is N or CRS, $Y^2$ is one of O, S, Se, Te, and $C(R^t)(CN)$, $Y^3$ is O, S, Se, or Te, $Y^4$ is N or $NR^{18a}$, $Y^5$ is $CR^{19a}$ or $C=CR^{20a}(CN)$, $Ar^{1a}$ and $Ar^{2a}$ are independently a substituted or unsubstituted C6 to C30 aryl group or a substituted or unsubstituted C3 to C30 heteroaryl group, $Ar^{1a}$ and $Ar^{2a}$ are independently present or linked with each other to form a ring, $R^{1a}$ to $R^{3a}$, $R^{11a}$, $R^{12a}$, $R^{15a}$ to $R^{20a}$, $R^{24a}$, $R^{25a}$, $R^h$, $R^i$, and $R^q$ to $R^t$ are independently hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, n1 is 0 or 1, m1 is 0 or 1, and m2 is an integer ranging from 0 to 4.

The light absorbing material represented by one of Chemical Formulae 8A-1 to 8A-4 may be for example one of compounds of Group 2 to Group 5, but is not limited thereto.

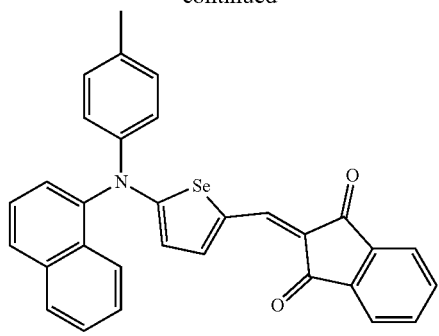
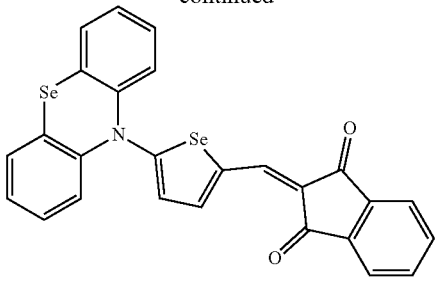
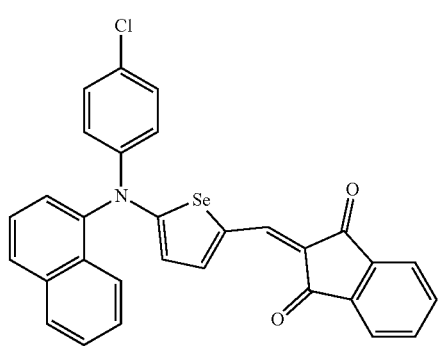
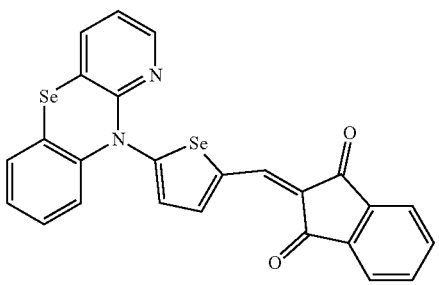
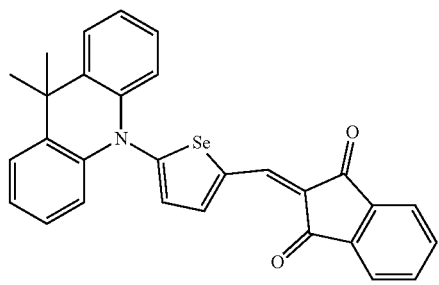
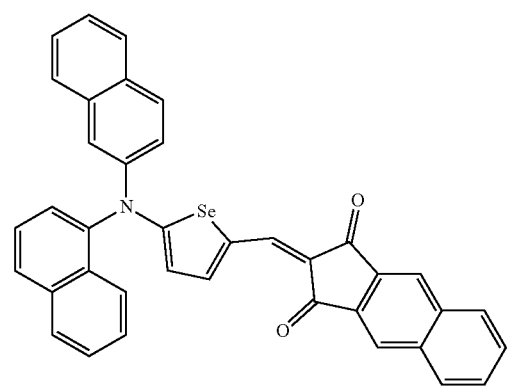
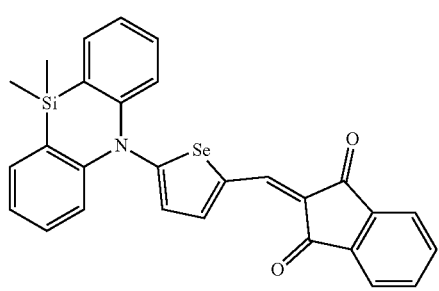
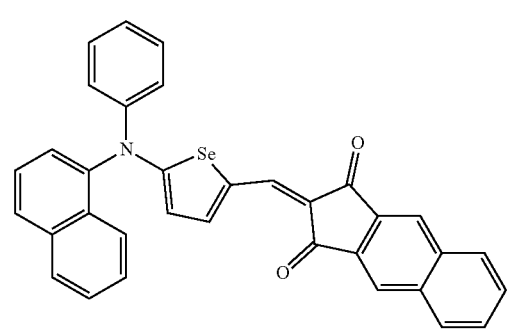
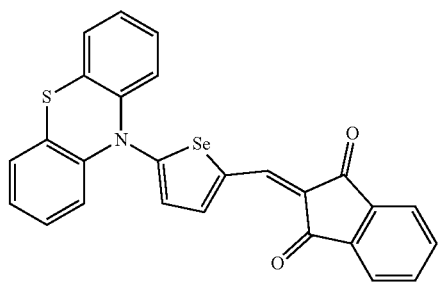
[Group 3]
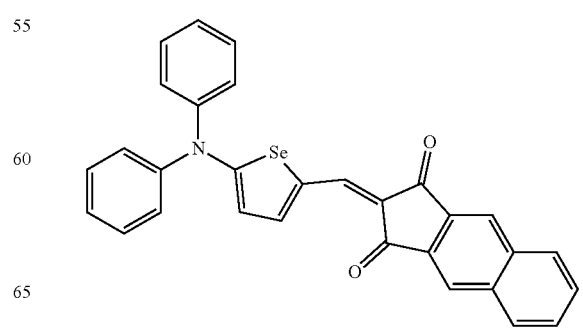

51
-continued
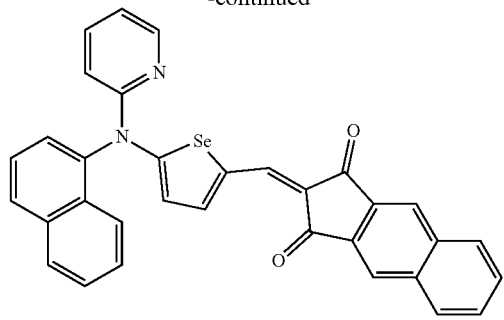
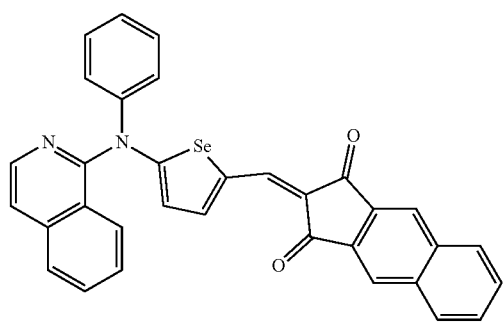
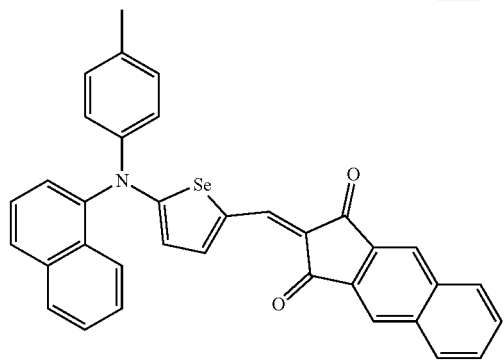
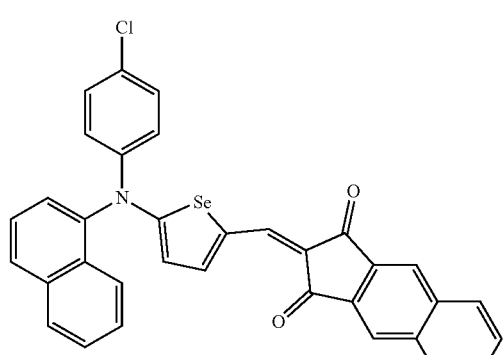
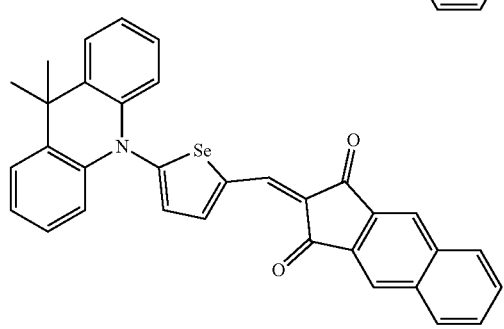
52
-continued
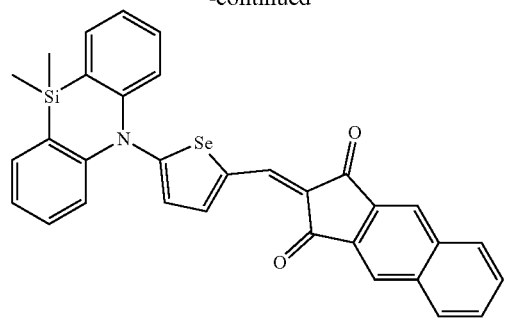
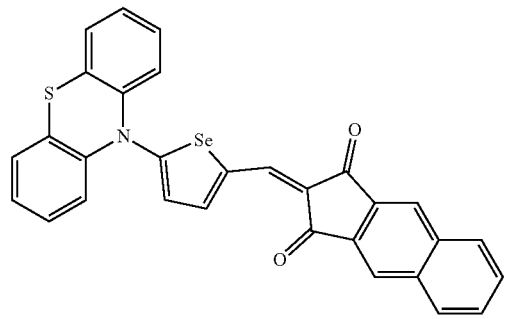
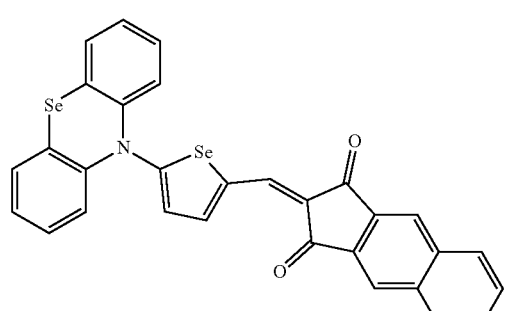
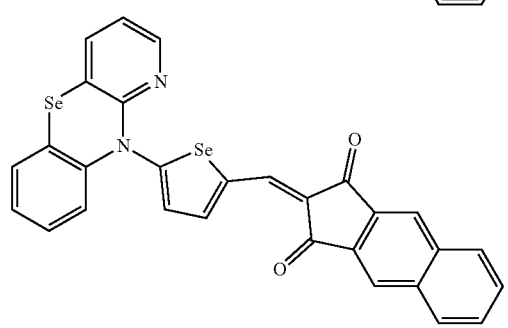
[Group 4]
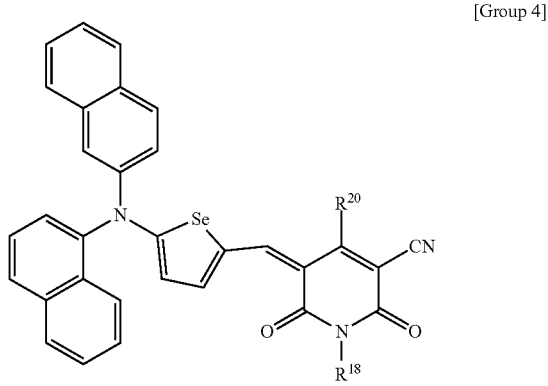

53
-continued
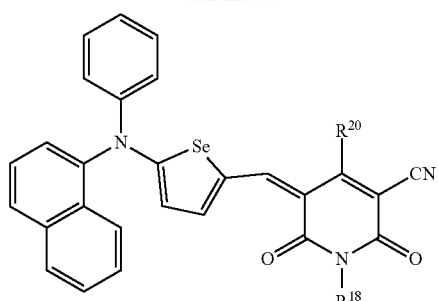
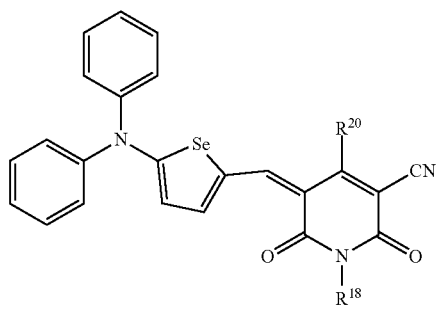
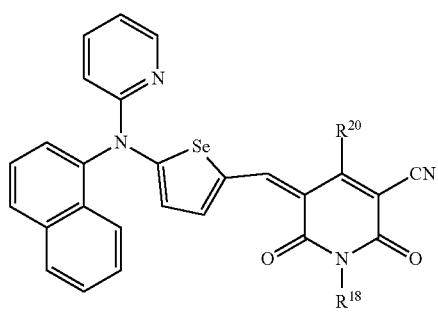
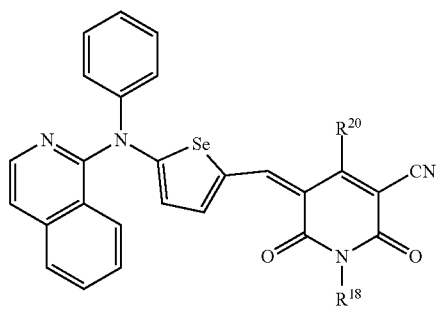
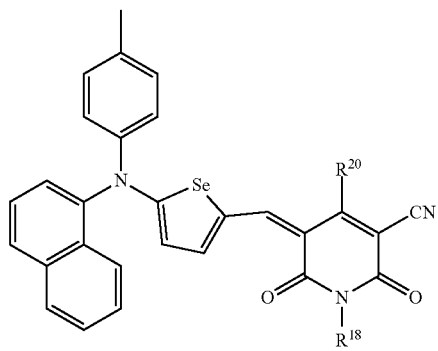
54
-continued
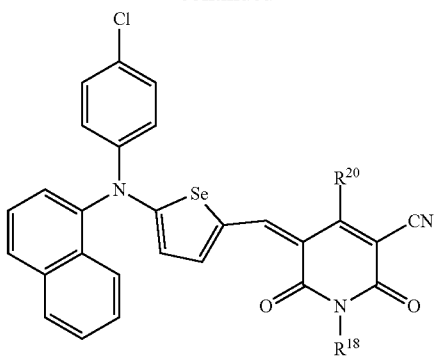
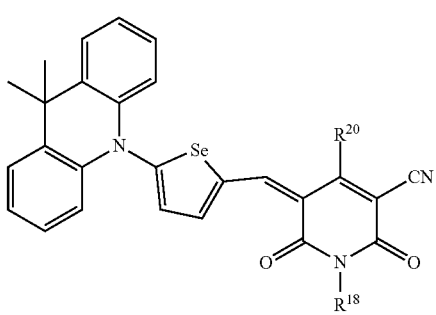
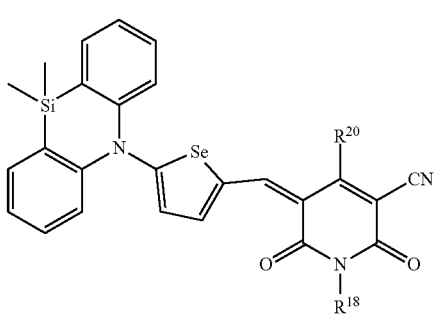
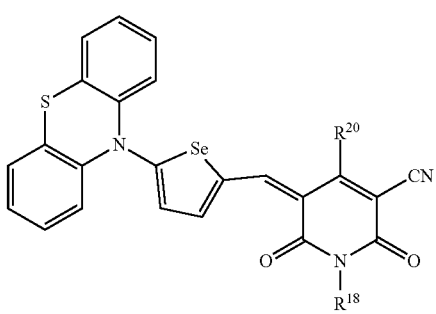
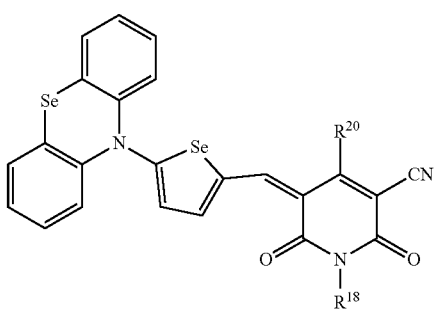

55
-continued
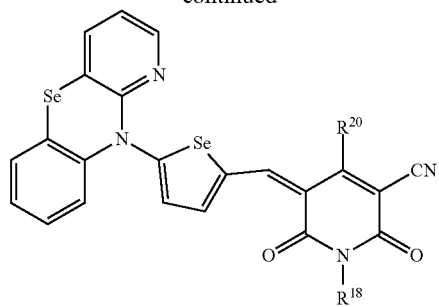
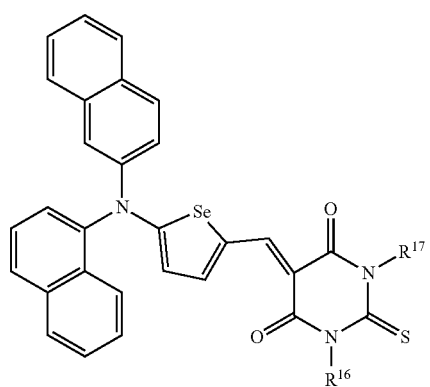
[Group 5]
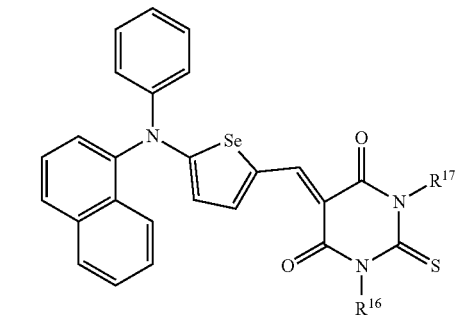
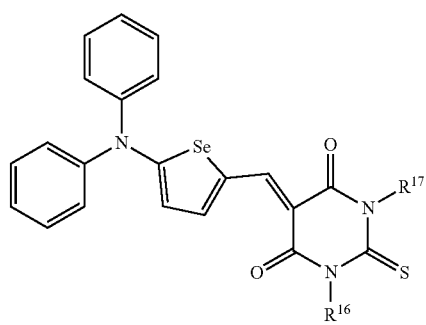
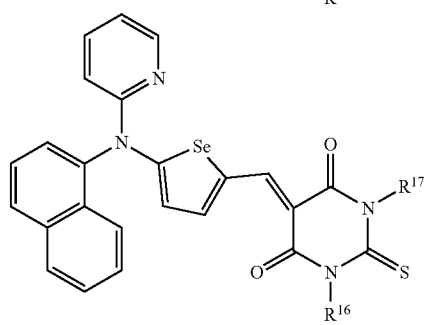
56
-continued
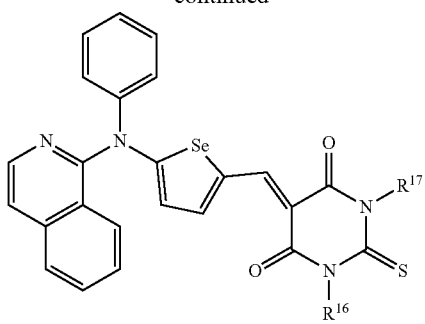
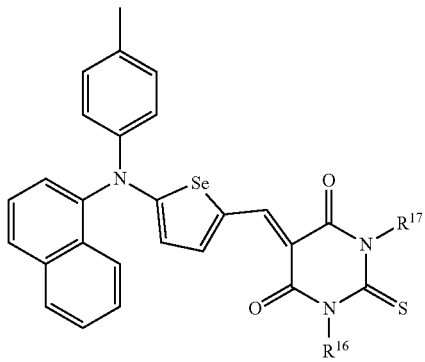
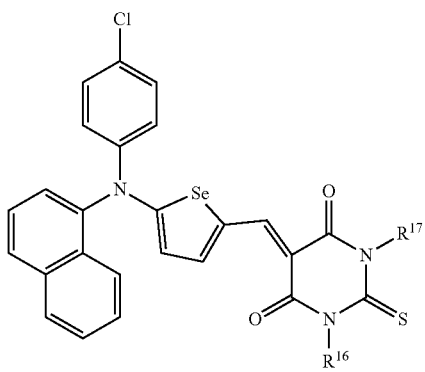
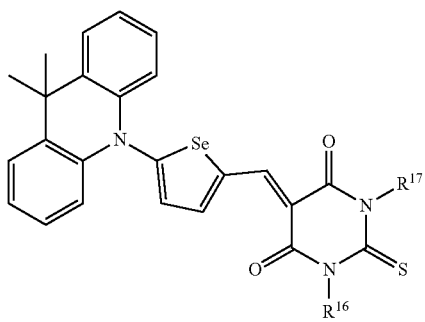
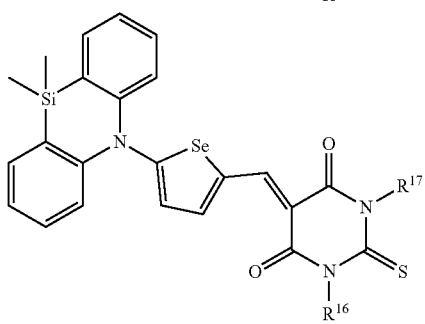

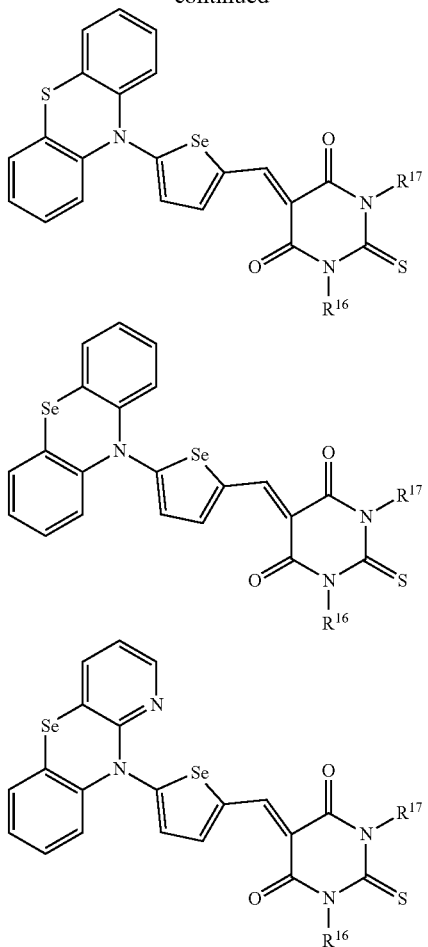

In Groups 2 to 5, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and $R^{16}$, $R^{17}$, $R^{18}$, and $R^{20}$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof.

The n-type semiconductor may include the fullerene derivative.

The fullerene derivative has an LUMO energy level, a HOMO energy level, and an bandgap energy which are effective for electrical matching with the aforementioned p-type semiconductor as described above.

The fullerene derivative may be designed to satisfy the electrical characteristics (LUMO energy level, HOMO energy level, and bandgap energy), and the specific structure of the fullerene derivative is the same as described above.

The fullerene derivative is effectively electrically matched with the p-type semiconductor as described above. In addition, the fullerene derivative has a structure substituted with a fused ring of a S-containing pentagonal ring and an aromatic ring and thus may increase a steric hindrance but decrease a π-conjugation system compared with the unsubstituted fullerene. Accordingly, the fullerene derivative may suppress an aggregation during the deposition compared with the unsubstituted fullerene (e.g., C60 fullerene) and thus may improve film-formation characteristics and reduce transformation of optical properties such as a transformation of an absorption wavelength region which may be caused by the aggregation.

The aforementioned p-type semiconductor and an n-type semiconductor including the fullerene derivative may be codeposited through sublimation to form an active layer, and thus the active layer may maintain inherent characteristics of the fullerene derivative without breaking and/or transforming a chemical bond of the fullerene derivative during the codeposition.

For example, the active layer including the fullerene derivative may have different light absorption characteristics from those of an active layer including unsubstituted fullerene (e.g., C60 fullerene), and thus abnormal absorption in a short wavelength region of a visible ray, for example, ranging from about 400 nm to about 500 nm may be reduced. For example, the active layer including the fullerene derivative may have a smaller absorption coefficient at a wavelength of 450 nm than that of an active layer including unsubstituted fullerene (e.g., C60 fullerene), and the absorption coefficient at a wavelength of 450 nm of the active layer including the fullerene derivative may be less than or equal to about ½ of that of the active layer including unsubstituted fullerene (e.g., C60 fullerene) at a wavelength of 450 nm.

Light absorption characteristics of the active layer may be expressed by combining those of the p-type semiconductor with those of the n-type semiconductor. For example, an absorption peak of an active layer including a p-type semiconductor selectively absorbing light in a wavelength region of about 500 nm to about 600 nm and an n-type semiconductor including the fullerene derivative may be easily separated compared with that the active layer including the p-type semiconductor selectively absorbing light in a wavelength region of about 500 nm to about 600 nm and an unsubstituted fullerene (e.g., C60 fullerene), and thus wavelength selectivity of the active layer may be increased. Accordingly, the active layer may be effectively used for an organic photoelectric device requiring the wavelength selectivity.

The active layer may include an intrinsic layer formed by codepositing the p-type semiconductor and the n-type semiconductor including the fullerene derivative and the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The active layer may further include a p-type layer and/or an n-type layer in addition to the intrinsic layer. The p-type layer may include the p-type semiconductor and the n-type layer may include the n-type semiconductor. For example, the active layer may include various combinations of a p-type layer/an I layer, an I layer/an n-type layer, a p-type layer/an I layer/a n-type layer, and the like.

The organic layer 30 may further include a charge auxiliary layer (not shown) between the first electrode 10 and the active layer and/or between the second electrode 20 and the active layer.

The charge auxiliary layer may make holes and electrons separated in the active layer be transported easily to improve efficiency.

The charge auxiliary layer may include at least one selected from a hole injection layer for facilitating hole injection, a hole transport layer for facilitating hole transport, an electron blocking layer for limiting and/or preventing electron transport, an electron injection layer for facilitating electron injection, an electron transport layer for facilitating electron transport, and a hole blocking layer for limiting and/or preventing hole transport.

The charge auxiliary layer may include for example an organic material, an inorganic material, or an organic/inorganic material. The organic material may be an organic material having hole or electron (injection, transportation, or blocking) characteristics and the inorganic material may be for example a metal oxide such as a molybdenum oxide, a tungsten oxide, or a nickel oxide.

The charge auxiliary layer may include for example the aforementioned fullerene derivative.

The organic photoelectric device 100 may further include an anti-reflection layer (not shown) on one surface of the first electrode 10 or the second electrode 20. The anti-reflection layer is disposed at a light incidence side and lowers light reflectance of incident light and thereby light absorbance is further improved. For example, when light enters from the first electrode 10, the anti-reflection layer may be disposed on one surface of the first electrode 10 while when light enters from the second electrode 20, the anti-reflection layer may be disposed on one surface of the second electrode 20.

The anti-reflection layer may include, for example a material having a refractive index of about 1.6 to about 2.5, and may include for example at least one of a metal oxide, a metal sulfide, and an organic material having a refractive index within the ranges. The anti-reflection layer may include, for example a metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as zinc sulfide; or an organic material such as an amine derivative, but is not limited thereto.

In the organic photoelectric device 100, when light enters from the first electrode 10 or second electrode 20 and the active layer absorbs light in a desired (and/or alternatively predetermined) wavelength region, excitons may be produced from the inside. The excitons are separated into holes and electrons in the active layer, and the separated holes are transported to an anode that is one of the first electrode 10 and the second electrode 20 and the separated electrons are transported to the cathode that is the other of the first electrode 10 and the second electrode 20 so as to flow a current.

The organic photoelectric device 100 may be applied to a solar cell, an image sensor, a photodetector, a photosensor, and an organic light emitting diode (OLED), but is not limited thereto.

The organic photoelectric device may be for example applied to an image sensor.

Hereinafter, an example of an image sensor including the photoelectric device is described referring to drawings. As an example of an image sensor, an organic CMOS image sensor is described.

Figure 2:
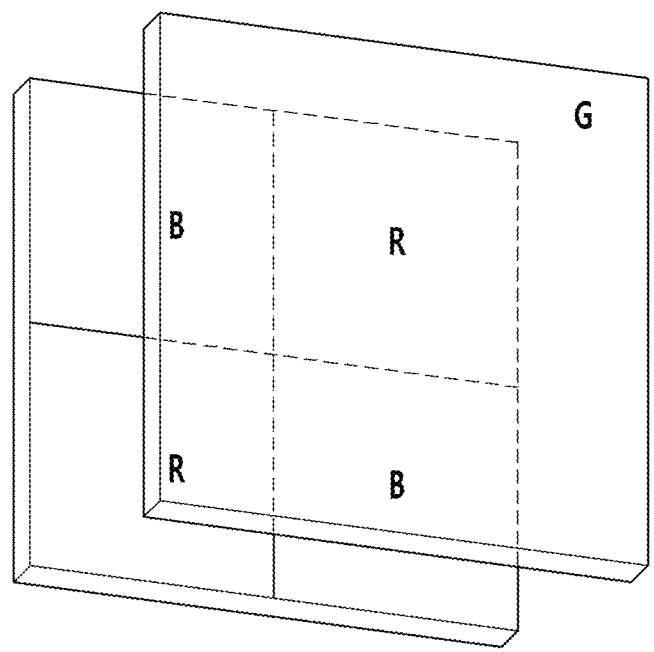
FIG. 2 is a top plan view schematically showing an organic CMOS image sensor according to an embodiment.
Figure 3:
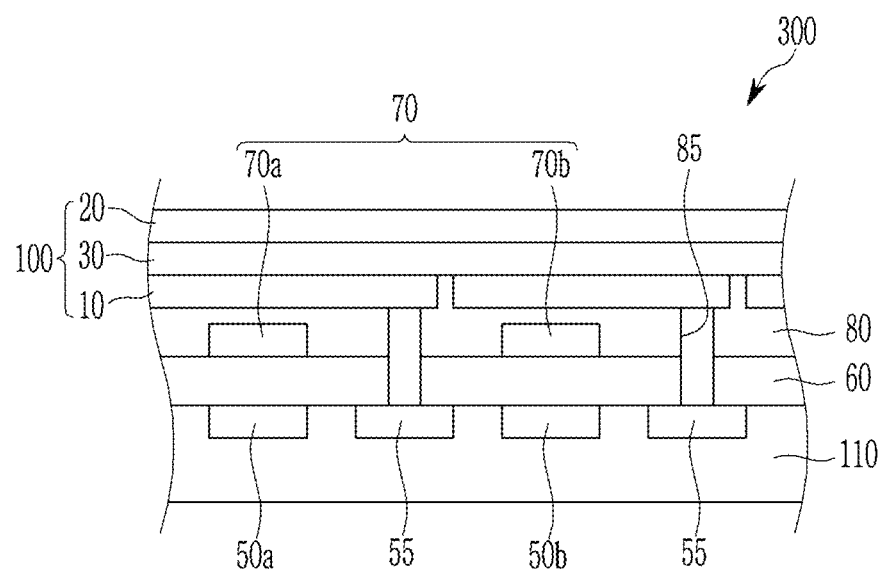
FIG. 3 is a cross-sectional view showing an example of an organic CMOS image sensor of FIG. 2.

FIG. 2 is a schematic top plan view of an organic CMOS image sensor according to an embodiment and FIG. 3 is a cross-sectional view showing one example of the organic CMOS image sensor of FIG. 2.

Referring to FIGS. 2 and 3, an organic CMOS image sensor 300 according to an example embodiment includes a semiconductor substrate 110 integrated with photo-sensing devices 50a and 50b, a transmission transistor (not shown) and a charge storage 55, a lower insulation layer 60, a color filter layer 70, an upper insulation layer 80, and an organic photoelectric device 100.

The semiconductor substrate 110 may be a silicon substrate, and is integrated with the photo-sensing devices 50a and 50b, the transmission transistor (not shown), and the charge storage 55. The photo-sensing devices 50a and 50b may be photodiodes.

The photo-sensing devices 50a and 50b, the transmission transistor, and/or the charge storage 55 may be integrated in each pixel, and as shown in the drawing, the photo-sensing devices 50a and 50b may be respectively included in a blue pixel and a red pixel and the charge storage 55 may be included in a green pixel.

The photo-sensing devices 50a and 50b sense light, the information sensed by the photo-sensing devices may be transferred by the transmission transistor, the charge storage 55 is electrically connected to the organic photoelectric device 100 that will be described later, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), or alloys thereof, but are not limited thereto. Further, it is not limited to the structure, and the metal wire and pad may be disposed under the photo-sensing device 50a and 50b.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70a formed in a blue pixel and a red filter 70b formed in a red pixel. In the present embodiment, a green filter is not included, but a green filter may be further included.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned organic photoelectric device 100 is formed on the upper insulation layer 80. The organic photoelectric device 100 includes the first electrode 10, the organic layer 30, and the second electrode 20 as described above. In the drawing, the first electrode 10, the organic layer 30, and the second electrode 20 are sequentially stacked, but this disclosure is not limited thereto, and for example they may be stacked in an order of the second electrode 20, the organic layer 30, and the first electrode 10.

The first electrode 10 and the second electrode 20 may be all light-transmitting electrodes and the organic layer 30 is the same as described above. The organic layer 30 may for example selectively absorb light in a green wavelength region and may replace a color filter of a green pixel.

Light in a green wavelength region of light that enters from the second electrode 20 is mainly absorbed by the organic layer 30 and photoelectrically converted and light in a remaining wavelength region is transmitted through the first electrode 10 and is sensed by the photo-sensing devices 50a and 50b.

Focusing lens (not shown) may be further formed on the organic photoelectric device 100. The focusing lens may control a direction of incident light and gather the light in one region. The focusing lens may have a shape of, for example, a cylinder or a hemisphere, but is not limited thereto.

As described above, the organic photoelectric device 100 has a stack structure thereby a size of an image sensor may be reduced to realize a down-sized image sensor.

In addition, the organic layer includes the fullerene derivative having optical absorption characteristics shifted toward a short wavelength as described above and thus may increase wavelength selectivity compared with the one including the unsubstituted fullerene (e.g., C60 fullerene).

In the drawings, the organic photoelectric device selectively absorbing light in a green wavelength region is for example stacked but this disclosure is not limited thereto. For example, an organic photoelectric device selectively absorbing light in a blue wavelength region may be stacked and a green photo-sensing device and a red photo-sensing device may be integrated in the semiconductor substrate 110 or an organic photoelectric device selectively absorbing light in a red wavelength region may be stacked and a green photo-sensing device and a blue photo-sensing device may be integrated in the semiconductor substrate 110.

Figure 4:
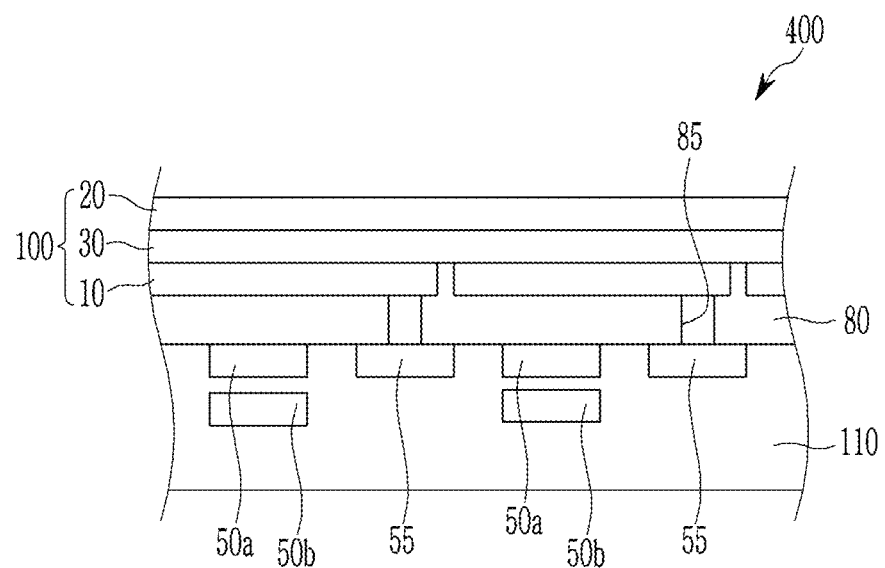
FIG. 4 is a cross-sectional view showing another example of an organic CMOS image sensor.

FIG. 4 is a cross-sectional view showing another example of the organic CMOS image sensor.

The organic CMOS image sensor 400 according to the present embodiment like the above embodiment includes a semiconductor substrate 110 integrated with photo-sensing devices 50a and 50b, a transmission transistor (not shown), and a charge storage 55, an upper insulation layer 80 having a through-hole 85, and an organic photoelectric device 100.

However, unlike the above embodiment, in the CMOS image sensor 400 according to the present embodiment unlike the above embodiment, the photo-sensing devices 50a and 50b are stacked in a vertical direction, but the color filter layer 70 is omitted. The photo-sensing devices 50a and 50b are electrically connected to charge storage (not shown) and their information may be transferred by the transmission transistor. The photo-sensing devices 50a and 50b may selectively absorb light in each wavelength region depending on a stacking depth.

Focusing lens (not shown) may be further formed on the organic photoelectric device 100. The focusing lens may control a direction of incident light and gather the light in one region. The focusing lens may have a shape of, for example, a cylinder or a hemisphere, but is not limited thereto.

As described above, the organic photoelectric device selectively absorbing light in a green wavelength region is stacked and the red photo-sensing device and the blue photo-sensing device are stacked, and thereby a size of an image sensor may be reduced to realize a down-sized image sensor.

In FIG. 4, the organic photoelectric device selectively absorbing light in a green wavelength region is for example stacked, but this disclosure is not limited thereto. For example, an organic photoelectric device selectively absorbing light in a blue wavelength region may be stacked and a green photo-sensing device and a red photo-sensing device may be integrated in the semiconductor substrate 110 or an organic photoelectric device selectively absorbing light in a red wavelength region may be stacked and a photo-sensing device and a blue photo-sensing device may be integrated in the semiconductor substrate 110.

Figure 5:
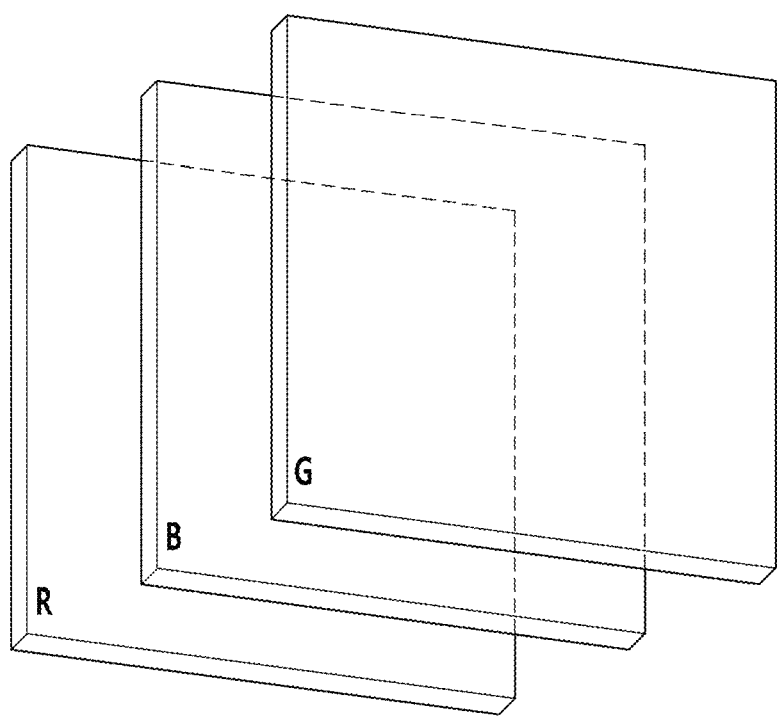
FIG. 5 is a top plan view schematically showing an organic CMOS image sensor according to another embodiment.
Figure 6:
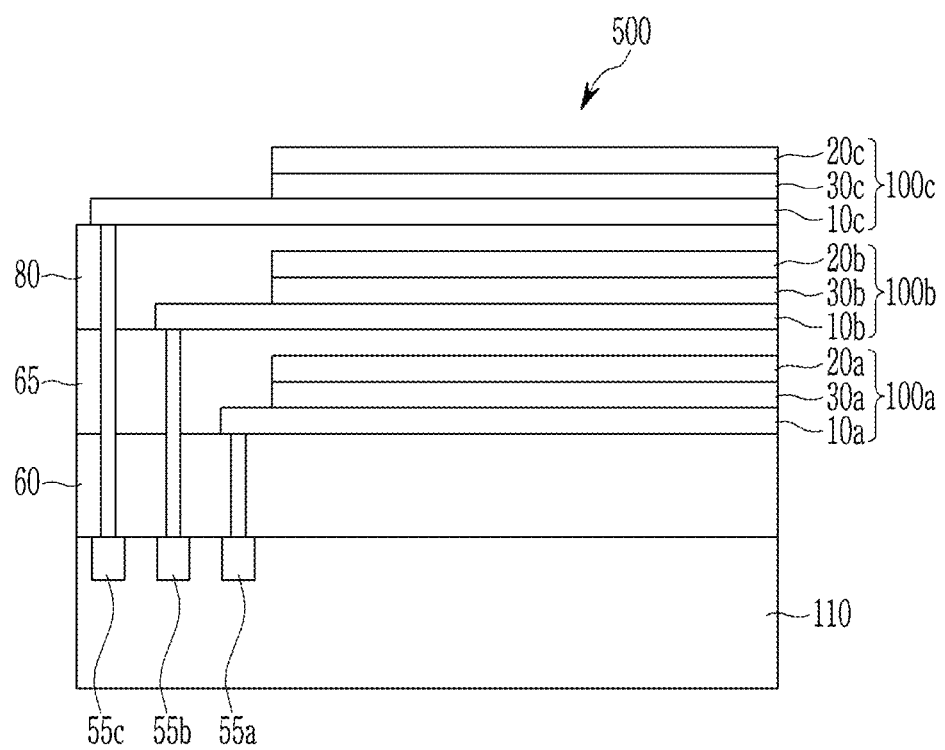
FIG. 6 is a cross-sectional view of the organic CMOS image sensor of FIG. 5, FIGS. 7 and 8 are graphs showing current-voltage curve lines (from first cycle to third cycle) measured by cyclic-voltammetry of each fullerene derivative according to Synthesis Example 2 and Comparative Synthesis Example 2.

FIG. 5 is a schematic top plan view showing an organic CMOS image sensor according to another embodiment and FIG. 6 is a cross-sectional view of the organic CMOS image sensor of FIG. 5.

The organic CMOS image sensor 500 according to the present embodiment includes an organic photoelectric device selectively absorbing light in a green wavelength region, an organic photoelectric device selectively absorbing light in a blue wavelength region, and an organic photoelectric device selectively absorbing light in a red wavelength region that are stacked.

The organic CMOS image sensor 500 according to the present embodiment includes a semiconductor substrate 110, a lower insulation layer 60, an intermediate insulation layer 65, an upper insulation layer 80, a first organic photoelectric device 100a, a second organic photoelectric device 100b, and a third organic photoelectric device 100c.

The semiconductor substrate 110 may be a silicon substrate, and is integrated with the transmission transistor (not shown) and the charge storages 55a, 55b, and 55c.

A metal line (not shown) and pad (not shown) are formed on the semiconductor substrate 110 and a lower insulation layer 60 is formed on the metal line and pad.

The first organic photoelectric device 100a is formed on the lower insulation layer 60.

The first organic photoelectric device 100a includes a first electrode 10a and a second electrode 20a facing each other and an organic layer 30a disposed between the first electrode 10a and the second electrode 20a. The first electrode 10a, the second electrode 20a, and the organic layer 30a are the same as described above and the organic layer 30a may selectively absorb light in one wavelength region of red, blue, and green. For example, the first organic photoelectric device 100a may be a red organic photoelectric device.

In the drawing, the first electrode 10a, the organic layer 30a, and the second electrode 20a are sequentially stacked, but this disclosure is not limited thereto, and for example they may be stacked in an order of the second electrode 20a, the organic layer 30a, and the first electrode 10a.

The intermediate insulation layer 65 is formed on the first organic photoelectric device 100a.

The second organic photoelectric device 100b is formed on the intermediate insulation layer 65.

The second organic photoelectric device 100b includes a first electrode 10b and a second electrode 20b facing each other and an organic layer 30b disposed between the first electrode 10b and the second electrode 20b. The first electrode 10b, the second electrode 20b, and the organic layer 30b are the same as described above and the organic layer 30b may selectively absorb light in one wavelength region of red, blue and green. For example, the second photoelectric device 100b may be a blue organic photoelectric device.

In the drawing, the first electrode 10b, the organic layer 30b, and the second electrode 20b are sequentially stacked, but this disclosure is not limited thereto, and for example they may be stacked in an order of the second electrode 20b, the organic layer 30b, and the first electrode 10b.

The upper insulation layer 80 is formed on the second organic photoelectric device 100b. The lower insulation layer 60, the intermediate insulation layer 65, and the upper insulation layer 80 have a plurality of through-holes exposing the charge storages 55a, 55b, and 55c.

The third organic photoelectric device 100c is formed on the upper insulation layer 80. The third organic photoelectric device 100c includes a first electrode 10c and a second electrode 20c facing each other and an organic layer 30c disposed between the first electrode 10c and the second electrode 20c. The first electrode 10c, the second electrode 20c, and the organic layer 30c are the same as described above and the organic layer 30c may selectively absorb light in one wavelength region of red, blue, and green. For example, the third organic photoelectric device 100c may be a green organic photoelectric device.

In the drawing, the first electrode 10c, the organic layer 30c, and the second electrode 20c are sequentially stacked, but this disclosure is not limited thereto, and for example they may be stacked in an order of the second electrode 20c, the organic layer 30c, and the first electrode 10c.

Focusing lens (not shown) may be further formed on the organic photoelectric device 100c. The focusing lens may control a direction of incident light and gather the light in one region. The focusing lens may have a shape of, for example, a cylinder or a hemisphere, but is not limited thereto.

In the drawing, the first organic photoelectric device 100a, the second organic photoelectric device 100b, and the third organic photoelectric device 100c are sequentially stacked, but the present disclosure is not limited thereto, and they may be stacked in various orders.

As described above, the first organic photoelectric device 100a, the second organic photoelectric device 100b, and the third organic photoelectric device 100c that absorb light in different wavelength regions are stacked, and thereby a size of an image sensor may be reduced to realize a down-sized image sensor.

The image sensor may be applied to, for example, various electronic devices such as a mobile phone or a digital camera, but is not limited thereto.

Figure 9:
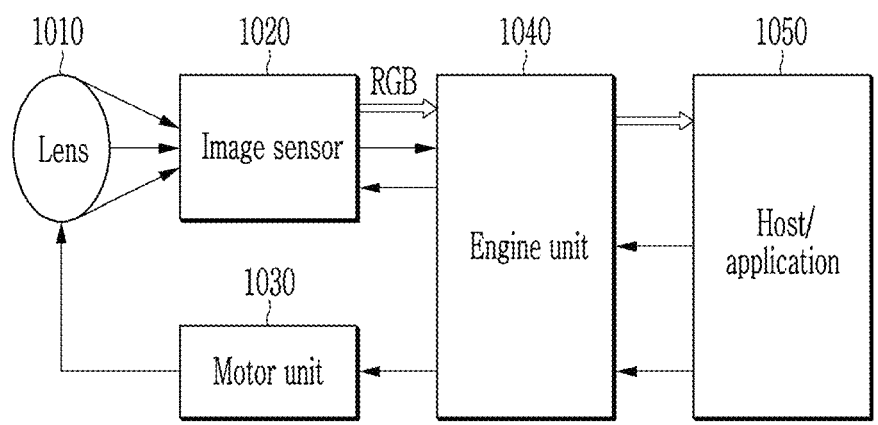
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor unit 1030, and an engine unit 1040. The image sensor 1020 may be one of image sensors according to embodiments shown in FIGS. 2 to 6.

The lens 1010 concentrates incident light on the image sensor 1020. The image sensor 1020 generates RGB data for received light through the lens 1010.

In some embodiments, the image sensor 1020 may interface with the engine unit 1040.

The motor unit 1030 may adjust the focus of the lens 1010 or perform shuttering in response to a control signal received from the engine unit 1040. The engine unit 1040 may control the image sensor 1020 and the motor unit 1030.

The engine unit 1040 may be connected to a host/application 1050.

Hereinafter, the embodiments are illustrated in more detail with reference to examples. However, these examples are non-limiting, and the scope of claims is not limited thereto.

SYNTHESIS EXAMPLES

Synthesis Example 1

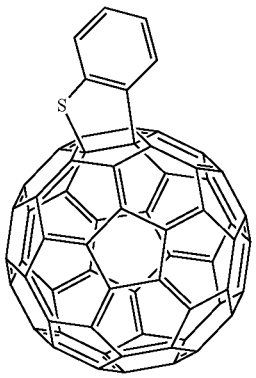

[Chemical Formula A]

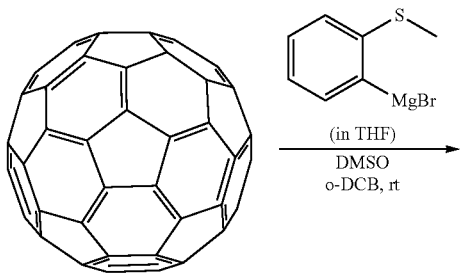

[Reaction Scheme A]

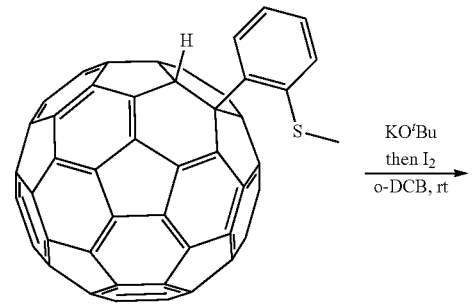

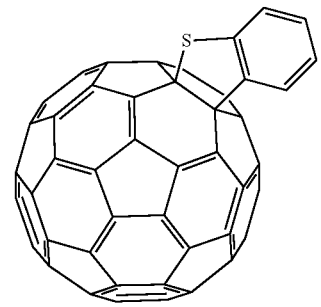

C60 (fullerene, 50.0 mg, 0.069 mmol) is dissolved in o-DCB (orthodichlorobenzene, 15.0 mL) under an Ar atmosphere, DMSO (0.1 mL, 1.0 mmol, 10.0 equiv.) is added thereto to obtain mixture, and while a temperature of the mixture is maintained a temperature at 25° C., and 2-methylthiophenyl magnesium bromide (0.1 mL, 1.3 mol/L solution, 0.13 mmol, 1.3 equiv.) is added thereto.

This solution is stirred at 25° C. for 40 minutes. Subsequently, a NH$_4$Cl aqueous solution (0.1 mL, 1.0 mol/L solution) is added thereto to complete a reaction. The solution is evaporated with an evaporator, and excess MeOH is added thereto to extract a solid component.

Then, the solid component is dissolved in carbon disulfide and then purified through a silica gel column (eluent: a mixture of carbon disulfide and hexane (in a volume ratio of 1:1)).

After evaporating the solvent from the obtained solution, solids therefrom are dissolved in toluene, and a product is separated by using Recycle HPLC (Buckyprep 4.6 φ×250 mm; eluent: toluene/2-propanol=8/2 in a volume ratio).

The product (20.0 mg, 23.0 μmol) is dissolved under an Ar atmosphere to obtain an o-DCB solution (2.0 mL), and while a temperature of the solution is maintained a temperature at 25° C., a THF solution of t-BuOK (potassium tert-butoxide, 1.0 M, 27.0 μL, 27.0 μmol) is added thereto. The obtained mixture is stirred at 25° C. for 20 minutes, and I$_2$ (iodine, 24.0 mg, 95.0 μmol) is added thereto.

After stirring the resultant for 1 hour, carbon disulfide is added to the obtained suspend solution, and solids are removed by passing through a silica gel column.

After evaporating the solvent from the obtained solution, the solids are dissolved in toluene, and a solution including a product and a by-product is separated using Recycle HPLC (Buckyprep 4.6 φ×250 mm; Eluent: toluene/2-propanol=8/2 (a volume ratio)). The solvent is evaporated from the solution to obtain a mixture of the product and the by-product.

The mixture is purified by silica gel column chromatography (Eluent: a mixture of carbon disulfide and hexane (a volume ratio of 1:1)) to obtain a solution. The solvent is evaporated from the solution to obtain a product. A yield is 5.4%.

$^1$H NMR (400 MHz, CDCl$_3$/CS$_2$=1:1): δ 8.01 (d, 1H), 7.52 (d, 1H), 7.44 (t, 1H), 7.35 (t, 1H).

Synthesis Example 2

[Chemical Formula B]

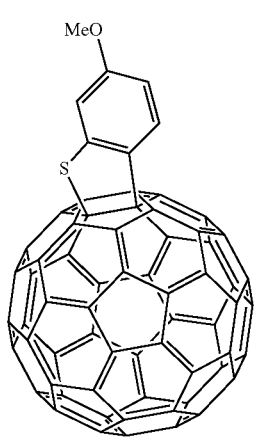

C60 (fullerene, 150.0 mg, 0.208 mmol) is dissolved in o-DCB (orthodichlorobenzene, 45.0 mL) under an Ar atmosphere, DMSO (0.3 mL, 3.1 mmol, 15.0 equiv.) is added thereto to obtain mixture, and while a temperature of the mixture is maintained a temperature at 25° C., and 2-methylthio-4-methoxyphenyl magnesium bromide (0.3 mL, 0.9 mol/L solution, 0.3 mmol, 1.5 equiv.) is added thereto.

This solution is stirred at 25° C. for 40 minutes. Subsequently, an NH$_4$Cl aqueous solution (0.2 mL, 1.0 mol/L solution) is added thereto to complete a reaction. The solution is evaporated with an evaporator, and excess MeOH is added thereto to extract solids.

Subsequently, the solids are dissolved in carbon disulfide and purified through a silica gel column (eluent: a mixture of carbon disulfide and hexane (a volume ratio of 1:1)) to obtain a solution. After evaporating the solvent from the obtained solution, the solids are dissolved in toluene, and a product is separated by using recycle HPLC (Buckyprep 4.6 φ×250 mm; Eluent: toluene/2-propanol=8/2 (a volume ratio)).

Subsequently, the product (10.0 mg, 12.0 μmol) is dissolved in o-DCB (2.0 mL) under an Ar atmosphere, and while a temperature of the solution is maintained a temperature at 25° C., a THF solution of t-BuOK (potassium tert-butoxide, 1.0 M, 24.0 μL, 24.0 μmol) is added thereto. The obtained mixture is stirred at 25° C. for 30 minutes, and I$_2$ (iodine, 18.0 mg, 69.0 μmol) is added thereto.

After stirring the resultant for 1 hour, carbon disulfide is added to the obtained suspend solution, and solids are removed by passing through a silica gel column.

After evaporating the solvent from the obtained solution, the solids are purified by using silica gel column chromatography (Eluent: a mixture of carbon disulfide and hexane (a volume ratio of 1:1)) to obtain a solution including the product. The solvent is evaporated from the solution to obtain a product. A yield is 27.7%.

$^1$H NMR (400 MHz, CDCl$_3$/CS$_2$=1:1) δ 7.85 (d, 1H), 6.99 (s, 1H), 6.86 (d, 1H), 3.92 (s, 3H).

Synthesis Example 3

[Chemical Formula C]

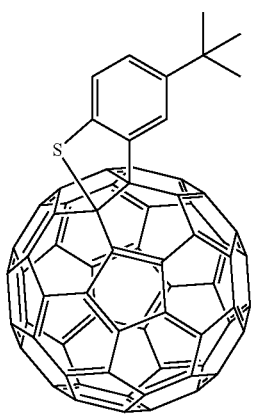

C60 (fullerene, 0.1 g, 0.139 mmol) is dissolved in o-DCB (orthodichlorobenzene, 30.0 mL) under an Ar atmosphere, DMSO (0.2 mL, 3.1 mmol, 15.0 equiv.) is added thereto to obtain mixture, and while a temperature of the mixture is maintained a temperature at 25° C., 2-methylthio-5-tert-butylphenylmagnesium bromide (0.2 mL, 1.0 mol/L solution, 0.2 mmol, 2 equiv.) is added thereto.

This solution is stirred at 25° C. for 40 minutes. Subsequently, a NH$_4$Cl aqueous solution (0.2 mL, 1.0 mol/L solution) is added thereto to complete a reaction. This solution is evaporated with an evaporator, and an excess MeOH is added thereto to extract solids.

Subsequently, the solids are dissolved in carbon disulfide and then, purified through a silica gel column y (eluent: a mixture of carbon disulfide and hexane (a volume ratio of 1:1)). After evaporating the solvent from the obtained solution, the solids are dissolved in toluene, and a product is separated by using Recycle HPLC (Buckyprep 4.6 φ×250 mm; Eluent: toluene/2-propanol=volume ratio of 8/2).

Subsequently, the product (10.0 mg, 12.0 µmol) is dissolved in o-DCB (2.0 mL) under an Ar atmosphere, and while a temperature of the solution is maintained a temperature at 25° C., a THF solution of t-BuOK (potassium tert-butoxide, 1.0 M, 24.0 µL, 24.0 µmol) is added thereto. The obtained mixture is stirred at 25° C. for 40 minutes, and I$_2$ (iodine, 18.0 mg, 69.0 µmol) is added thereto.

After stirring the resultant for 1 hour, carbon disulfide is added to the obtained suspend solution, and solids are removed by passing through a silica gel column.

After evaporating the solvent from the obtained solution, the solids are purified by using silica gel column chromatography (eluent: a mixture of carbon disulfide and hexane (volume ratio of 1:1)) to obtain a solution including the product. The solvent is evaporated from the solution to obtain a product. A yield is 18.0%.

$^1$H NMR (400 MHz, CDCl$_3$/CS$_2$=1:1): δ 7.54 (s, 1H), 7.30 (s, 1H), 1.48 (s, 9H), 1.44 (s, 9H).

Synthesis Example 4

[Chemical Formula D]

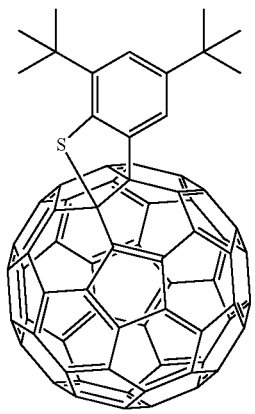

The same synthesis as Synthesis Example 3 is performed except that 2-methylthio-3,5-di-tert-butylphenyl magnesium bromide is used instead of the 2-methylthio-5-tert-butylphenyl magnesium bromide in Synthesis Example 3. A yield is 17.2%.

$^1$H NMR (400 MHz, CDCl$_3$/CS$_2$=1:1): δ 7.54 (s, 1H), 7.30 (s, 1H), 1.48 (s, 9H), 1.44 (s, 9H).

Synthesis Example 5

[Chemical Formula E]

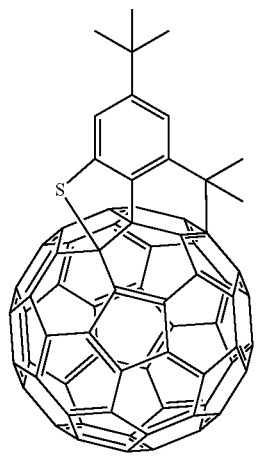

The same synthesis as Synthesis Example 3 is performed except that 2-methylthio-4,6-di-tert-butyl phenyl magnesium bromide is used instead of the 2-methylthio-5-tert-butylphenyl magnesium bromide in Synthesis Example 3. A yield is 17.6%.

$^1$H NMR (400 MHz, CDCl$_3$/CS$_2$=1:1): δ 7.84 (s, 1H), 7.44 (s, 1H), 1.47 (s, 9H), 1.44 (s, 9H).

Comparative Synthesis Example 1

[Chemical Formula F]

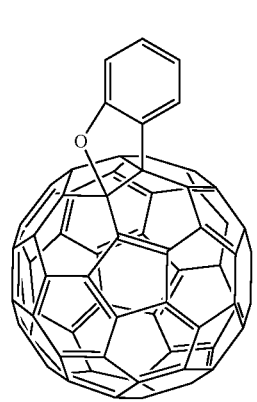

30.0 mg of a compound represented by Chemical Formula F is obtained by using 0.2 g of chlorofullerenes (C60Cl6) with reference to a synthesis method of Org. Biomol. Chem., 2003, 1, 1764 and J. Mater. Chem. A, 2017, 5, 2774-2783. A yield is 23.0%.

Data of $^1$H NMR perfectly correspond with those which are described in Org. Biomol. Chem., 2003, 1, 1764-1768.

Comparative Synthesis Example 2: Known Compound of Non-Patent Reference (J. Mater. Chem. A, 2017, 5, 2774)

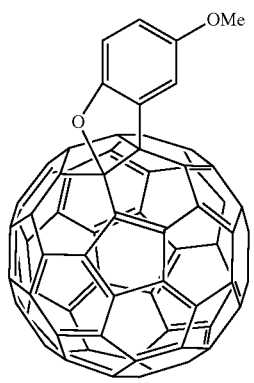

[Chemical Formula G]

0.1 g of N-tosyl[1,2]aziridino[60]fullerene (C60NTs) and 21.0 mg (1.5 equivalents) of 4-methoxylphenol are added to 11 mL of 1,2-dichlorobenzene (ODCB) under a nitrogen atmosphere and then stirred at room temperature (25° C.) for 10 minutes. Subsequently, 1.0 µL of trifluoromethane sulfonic acid (TfOH) is added thereto, and the obtained mixture is stirred at 100° C. for 12 hours. The resultant is cooled down to room temperature and then, purified through a silica gel column (a solvent: $CS_2$) and concentrated. Then, the obtained product is dissolved in toluene, and a product therein is separated with recycle HPLC (a solvent: toluene, a column: Bucky prep) to obtain 54.0 mg of a compound represented by Chemical Formula G. A yield is 56.6%.

$^1$H NMR (400 MHz, $CDCl_3/CS_2$): δ 7.54 (d, 1H), 7.53 (s, 1H), 7.30 (d, 1H), 3.92 (s, 3H).

Comparative Synthesis Example 3

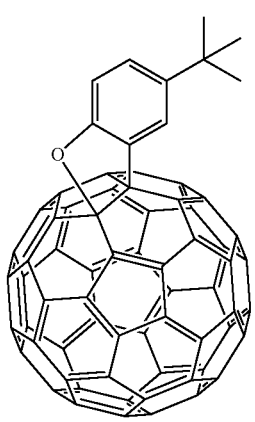

[Chemical Formula H]

0.1 g of N-tosyl[1,2]aziridino[60]fullerene (C60NTs) and 25.0 mg (1.5 equivalent) of 4-t-butylphenol are added to 11 ml of 1,2-dichlorobenzene (ODCB) under a nitrogen atmosphere and then, stirred at room temperature for 10 minutes. Subsequently, 1.0 µL of trifluoromethane sulfonic acid (TfOH) is added thereto, and the obtained mixture is stirred at 100° C. for 12 hours. The resultant is cooled down to room temperature and then, purified through a silica gel column (a solvent: $CS_2$) and concentrated. Then, the obtained product is dissolved in toluene, and a product therein is separated with recycled HPLC (a solvent: toluene, a column: Bucky prep) to obtain 44.0 mg of a compound represented by Chemical Formula H. A yield is 45.4%.

Data of $^1$H NMR perfectly correspond with those which are described in J. Am. Chem. Soc. 2011, 133, 2402-2405.

Comparative Synthesis Example 4

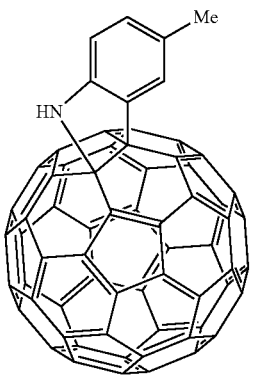

[Chemical Formula I]

The same synthesis as Comparative Synthesis Example 3 is performed except that p-toluidine is used instead of the 4-t-butylphenol, and the reaction time is changed from 12 hours in Comparative Synthesis Example 3 into 48 hours. A yield is 36.6%.

$^1$H NMR (400 MHz, $CDCl_3/CS_2$): 7.60 (d, 1H), 7.19 (dd, 1H), 7.03 (d, 1H), 5.59 (brs, 1H), 1.44 (s, 3H).

Unsubstituted C60 Fullerene

C60 fullerene (tradename nanom purple ST, Frontier Carbon Corporation) is used.

Example 1: Manufacture of Organic Photoelectric Device

An approximately 150 nm-thick anode is formed on a glass substrate by sputtering ITO. A 100 nm-thick active layer is formed by co-depositing the fullerene derivative (n-type semiconductor compound) represented by Chemical Formula A according to Synthesis Example 1 and a compound represented by Chemical Formula J (p-type semiconductor compound) on the anode in a volume ratio of 1:1. A molybdenum oxide ($MoO_x$, 0<x≤3) thin film is laminated with a thickness of 10 nm as a charge auxiliary layer. Subsequently, ITO is sputtered on the molybdenum oxide thin film to form a cathode with a thickness of 7 nm to manufacture an organic photoelectric device.

[Chemical Formula J]

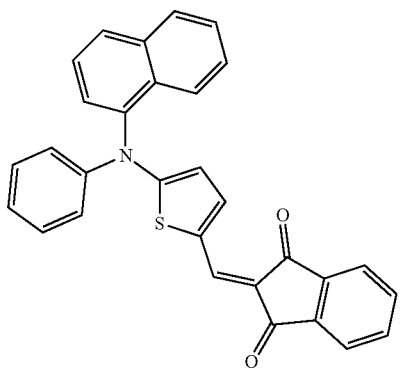

Examples 2 to 5 and Comparative Examples 1 to 5: Manufacture of Organic Photoelectric Device Organic photoelectric devices according to Examples 2 to 5 and Comparative Examples 1 to 4 are manufactured according to the same method as Example 1 except that each fullerene derivative according to Synthesis Examples 2 to 5 and Comparative Synthesis Examples 1 to 4 is used instead of the fullerene derivative represented by Chemical Formula A according to Synthesis Example 1.

An organic photoelectric device according to Comparative Example 5 is manufactured according to the same method as Example 1 except that unsubstituted C60 fullerene is used instead of the fullerene derivative represented by Chemical Formula A according to Synthesis Example 1.

Examples 6 to 10 and Comparative Examples 6 to 10: Manufacture of Organic CMOS Image Sensor (OCIS)

The organic photoelectric devices according to Examples 1 to 5 and Comparative Examples 1 to 5 are respectively disposed as the organic photoelectric device 100 in FIG. 3 so as to manufacture image sensors having the structure shown in FIG. 3.

Evaluations

Evaluation I: Current-Voltage Characteristics of Cyclic-Voltammetry

Electron acceptability of the fullerene derivatives obtained in Synthesis Examples 1 to 5 and Comparative Synthesis Examples 1 to 4 is evaluated by obtaining a current-voltage curve line through cyclic-voltammetry (CV). The cyclic-voltammetry is measured under the following conditions.

Solvent: o-DCB (orthodichlorobenzene)
Electrolyte: TBATFSI (tetrabutyl ammonium bis(trifluoromethanesulfonyl)imide)
Scan rate: 0.1 V/sec
Working and counter electrode: Pt
Ref. electrode: Ag/Ag$^+$ The measurement results are shown in Table 1.

TABLE 1

|  | 1$^{st}$ reduction peak (V) | 2$^{nd}$ reduction peak (V) | 3$^{rd}$ reduction peak (V) |
|---|---|---|---|
| Synthesis Example 1 | −1.14 | −1.48 | −1.86 |
| Synthesis Example 2 | −1.15 | −1.49 | −1.93 |

TABLE 1-continued

|  | 1$^{st}$ reduction peak (V) | 2$^{nd}$ reduction peak (V) | 3$^{rd}$ reduction peak (V) |
|---|---|---|---|
| Synthesis Example 3 | −1.14 | −1.51 | −2.02 |
| Synthesis Example 4 | −1.14 | −1.51 | −2.02 |
| Synthesis Example 5 | −1.14 | −1.51 | −2.02 |
| Comparative Synthesis Example 1 | −1.13 | No peak | No peak |
| Comparative Synthesis Example 2 | −1.12 | No peak | No peak |
| Comparative Synthesis Example 3 | −1.13 | No peak | No peak |
| Comparative Synthesis Example 4 | −1.16 | −1.52 | No peak |

Figure 7:
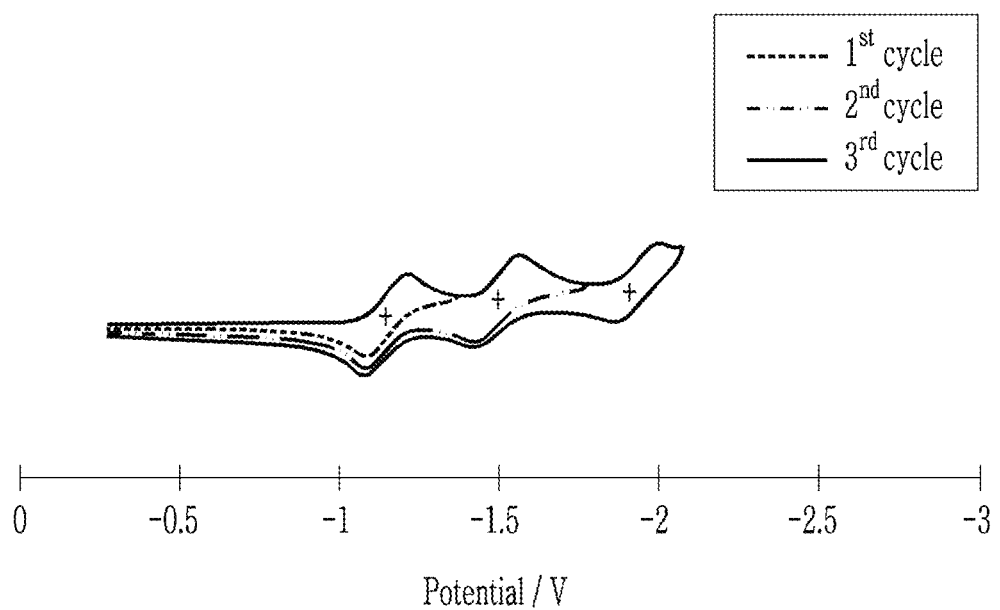
Figure 8:
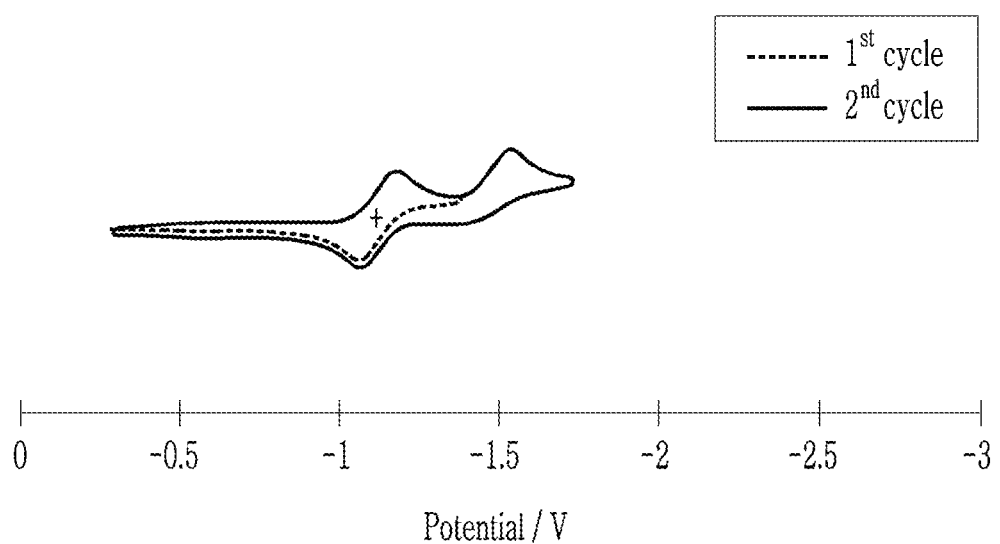

Referring to Table 1, the fullerene derivatives according to Synthesis Examples 1 to 5 exhibit reduction peaks up to the third cycle when measured through the cyclic-voltammetry, which exhibits that the fullerene derivatives have reversibility. However, the fullerene derivatives according to Comparative Synthesis Examples 1 to 3 exhibit no reduction peak from the second cycle, which exhibits that the fullerene derivatives have irreversibility, and the fullerene derivative according to Comparative Synthesis Example 4 exhibits no reduction peak from the third cycle, which exhibits that the fullerene derivative has irreversibility. In this way, the reversible peaks shown in the current-voltage curve line means excellent electron acceptability. When the electron acceptability is high, charges are effectively stored in a compound and transported, so that mobility may be improved. When this electron acceptability effect is improved, external quantum efficiency (EQE) of a device may be improved. FIGS. 7 and 8 are graphs showing current-voltage curve lines (from the first to third cycles) measured by cyclic-voltammetry of each fullerene derivative according to Synthesis Example 2 and Comparative Synthesis Example 2, respectively. Referring to FIG. 7, the fullerene derivative according to Synthesis Example 2 substantially exhibits a point-symmetrical waveform, even though three electrons are reduced. Accordingly, the fullerene derivative according to Synthesis Example 2 is stable, even though three electrons are reduced.

On the contrary, referring to FIG. 8, the fullerene derivative according to Comparative Synthesis Example 2 exhibits no point-symmetrical oxidation-reduction waveform around −1.5 V but a small peak waveform at −0.5 to −0.7 V when two electrons are reduced. Accordingly, the fullerene derivative according to Comparative Synthesis Example 2 exhibits no point-symmetrical waveform when the second electron is reduced. Accordingly, the fullerene derivative according to Comparative Synthesis Example 2 becomes unstable after two electrons are reduced.

FIG. 2(b) of an article of J. Mater. Chem. A, 2017, 5, 2774 to 2783 exhibits a current-voltage curve line of a similar structure (a substituent for Ar in Chemical Formula 1 is a methyl group, Material 6) to that of Comparative Synthesis Example 3 (a substituent for Ar in Chemical Formula 1 is tBu) which is measured through cyclic-voltammetry. Referring to FIG. 2(b) of the article, an oxidation-reduction peak of CV is not symmetrical after two electrons are reduced. Accordingly, Material 6 of the article becomes unstable after three electrons are reduced.

Evaluation II: EQE Characteristics

The external quantum efficiency of the organic photoelectric devices according to Examples 1 to 5 and Comparative Examples 1 to 3 is evaluated. The external quantum efficiency is evaluated by using an IPCE measurement system (McScience Inc., Korea). First, each of the organic photoelectronic devices of Examples 1 to 5 and Comparative Example 1 to 3 is mounted in the IPCE measurement system after calibrating the IPCE measurement system by using a Si photodiode (Hamamatsu Photonics K.K., Japan), and then external quantum efficiency of the organic photoelectronic devices is measured in a wavelength range of about 350 to 750 nm. The devices are measured with respect to external quantum efficiency when a bias of 3 V is applied thereto after heat-treated at 170° C. for 3 hours before mounted on an equipment. The results of the organic photoelectric devices according to Example 1 and Comparative Examples 1 to 3 are shown in Table 2.

TABLE 2

|  | 3V-EQE (Green) (%) |
|---|---|
| Example 1 | 60 |
| Comparative Example 1 | 50 |
| Comparative Example 2 | 39 |
| Comparative Example 3 | 39 |

Referring to Table 2, EQE in a green region of the organic photoelectric device according to Example 1 is improved by 10% or greater compared with those of the organic photoelectric devices according to Comparative Examples 1 to 3. The reason is that the fullerene derivative of Synthesis Example 1 around a p-type semiconductor compound of an electron-donating group efficiently accepts electrons generated there and transports them.

Evaluation III: Energy Level and Bandgap

Each fullerene derivative according to Synthesis Examples 1 to 5 and Comparative Synthesis Examples 1 to 4 is deposited to form a thin film, and each thin film is calculated with respect to an HOMO energy level, a LUMO energy level, and a bandgap in a method of ⌈Gaussian 09 program⌋ according to a B3LYP/6-G(d) level theory described in ⌈M. J. Frisch, et al., Gaussian 09, Revision D.01; Gaussian, Inc.: Wallingford, C T 2009⌋. The results are shown in Table 3.

TABLE 3

|  | HOMO (eV) | LUMO (eV) | Bandgap (eV) |
|---|---|---|---|
| Synthesis Example 1 | −5.71 | −3.21 | 2.50 |
| Synthesis Example 2 | −5.71 | −3.21 | 2.50 |
| Synthesis Example 3 | −5.71 | −3.21 | 2.50 |
| Synthesis Example 4 | −5.71 | −3.21 | 2.50 |
| Synthesis Example 5 | −5.71 | −3.21 | 2.50 |
| Comparative Synthesis Example 1 | −5.80 | −3.22 | 2.58 |
| Comparative Synthesis Example 2 | −5.80 | −3.22 | 2.58 |
| Comparative Synthesis Example 3 | −5.80 | −3.22 | 2.58 |
| Comparative Synthesis Example 4 | −5.79 | −3.21 | 2.58 |

Referring to Table 3, the fullerene derivatives according to Synthesis Examples 1 to 5 exhibit a shallow HOMO energy level compared with the fullerene derivatives according to Comparative Synthesis Examples 1 to 4. The fullerene derivatives according to Synthesis Examples 1 to 5 exhibit a shallow HOMO energy level, a narrow bandgap, and a wide absorption wavelength range and accordingly, may be usefully used for an image sensor or a solar cell.

Evaluation IV: Blue Light Absorption Characteristics

Each fullerene derivative according to Synthesis Examples 1 to 5 and an unsubstituted fullerene are deposited to form each thin film, and then the light absorption characteristics of each thin film are evaluated. The light absorption characteristics are evaluated by measuring absorption coefficients of a wavelength in an ultraviolet visible-near-infrared light region by using a UV-Vis spectrophotometer (Shimadzu Corp.). The results are shown in Table 4.

TABLE 4

|  | Absorption coeff. (450 nm) | Standard value |
|---|---|---|
| Synthesis Example 1 | 42,000 | 0.76 |
| Synthesis Example 2 | 32,458 | 0.59 |
| Synthesis Example 3 | 29,507 | 0.54 |
| Synthesis Example 4 | 23,571 | 0.43 |
| Synthesis Example 5 | 23,571 | 0.43 |
| unsubstituted fullerene | 55,056 | 1.00 |

In Table 4, the standard values are values converted with a reference to the unsubstituted fullerene.

Referring to Table 4, the thin films respectively including the fullerene derivatives according to Synthesis Examples 1 to 5 show small absorption coefficients at about 450 nm (blue wavelength region) compared with the thin film including the unsubstituted fullerene. Absorption in the blue wavelength region (about 450 nm) is known to be a peak caused by C60 aggregation (Journal of Molecular Structure 526 2000 25-29). From the results, the fullerene derivatives according to Synthesis Examples 1 to 5 show no abnormal light absorption characteristics in a short wavelength of a visible ray due to aggregation.

Evaluation V: Thermal Stability

The sublimation temperatures of the fullerene derivatives according to Synthesis Examples 1 to 5 and the unsubstituted fullerene are measured. $T_s$(° C.) (−10 wt %) and $T_s$(° C.) (−50 wt %) are measured by thermogravimetric analysis (TGA) by increasing temperatures under a high vacuum of less than or equal to 0.1 Pa. The results of Synthesis Examples 1 to 5 and the unsubstituted fullerene are shown in Table 5.

TABLE 5

|  | $T_s$ (° C.) (−10 wt %) | $T_s$ (° C.) (−50 wt %) |
|---|---|---|
| Synthesis Example 1 | 440 | 490 |
| Synthesis Example 2 | 430 | 490 |
| Synthesis Example 3 | 400 | 490 |
| Synthesis Example 4 | 400 | 450 |
| Synthesis Example 5 | 400 | 450 |
| unsubstituted fullerene | 450 | 500 |

* $T_s$ (° C.) (−10 wt %): a temperature at which a sample exhibits a weight loss of 10 wt %
* $T_s$ (° C.) (−50 wt %): a temperature at which a sample exhibits a weight loss of 50 wt %

Referring to Table 5, that the fullerene derivatives according to Synthesis Examples 1 to 5 are depositable compounds by sublimation, like the unsubstituted fullerene.

While this disclosure has been described in connection with what is presently considered to be practical example embodiments, it is to be understood that inventive concepts are not limited to the disclosed embodiments, but, on the contrary, are intended to cover various modifications and equivalent arrangements included within the spirit and scope of the appended claims.

DESCRIPTION OF SYMBOLS

100: organic photoelectric device
10: first electrode
20: second electrode
30: organic layer
300, 400, 500: organic CMOS image sensor

What is claimed is:

1. A fullerene derivative comprising:
a substituent represented by Chemical Formula 1,

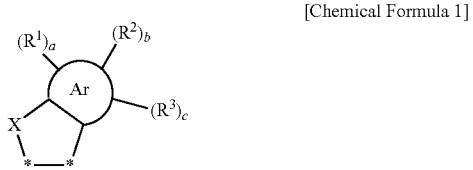

[Chemical Formula 1]

wherein, in Chemical Formula 1,
X is S,
Ar is a benzene ring, a naphthalene ring, an anthracene ring, a phenanthrene ring, a pyrene ring, or a triphenylene ring,
$R^1$ to $R^3$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, a halogen, a cyano group, or a combination thereof,
a, b, and c are independently an integer of 1 to 3, and
*—* is a linking portion with a fullerene core,
wherein the fullerene derivative exhibits a reversible peak in the current-voltage curve line of cyclic-voltammetry (CV).

2. The fullerene derivative of claim 1, wherein
in Chemical Formula 1, at least one of $R^1$ to $R^3$ is a linear substituent or a branched substituent,
the linear substituent is selected from a substituted or unsubstituted C1 to C20 linear alkyl group, a substituted or unsubstituted C2 to C20 linear alkenyl group, a substituted or unsubstituted C2 to C20 linear alkynyl group, a substituted or unsubstituted C1 to C20 linear heteroalkyl group, a substituted or unsubstituted C2 to C20 linear heteroalkenyl group, a substituted or unsubstituted C2 to C20 linear heteroalkynyl group, or a combination thereof, and
the branched substituent is selected from a substituted or unsubstituted C3 to C20 branched alkyl group, a substituted or unsubstituted C3 to C20 branched alkenyl group, a substituted or unsubstituted C3 to C20 branched alkynyl group, a substituted or unsubstituted C3 to C20 branched heteroalkyl group, a substituted or unsubstituted C3 to C20 branched heteroalkenyl group, a substituted or unsubstituted C3 to C20 branched heteroalkynyl group, or a combination thereof.

3. The fullerene derivative of claim 2, wherein
in Chemical Formula 1,
at least one of $R^1$ to $R^3$ is the linear substituent, and
at least one of $R^1$ to $R^3$ is the branched substituent.

4. The fullerene derivative of claim 1, wherein
in Chemical Formula 1, at least two of $R^1$ to $R^3$ are a linear substituent or a branched substituent,
the linear substituent is selected from a substituted or unsubstituted C1 to C20 linear alkyl group, a substituted or unsubstituted C2 to C20 linear alkenyl group, a substituted or unsubstituted C2 to C20 linear alkynyl group, a substituted or unsubstituted C1 to C20 linear heteroalkyl group, a substituted or unsubstituted C2 to C20 linear heteroalkenyl group, a substituted or unsubstituted C2 to C20 linear heteroalkynyl group, or a combination thereof, and
the branched substituent is selected from a substituted or unsubstituted C3 to C20 branched alkyl group, a substituted or unsubstituted C3 to C20 branched alkenyl group, a substituted or unsubstituted C3 to C20 branched alkynyl group, a substituted or unsubstituted C3 to C20 branched heteroalkyl group, a substituted or unsubstituted C3 to C20 branched heteroalkenyl group, a substituted or unsubstituted C3 to C20 branched heteroalkynyl group, or a combination thereof.

5. The fullerene derivative of claim 1, wherein
in Chemical Formula 1, at least one of $R^1$ to $R^3$ is a branched substituent represented by Chemical Formula 1-1:

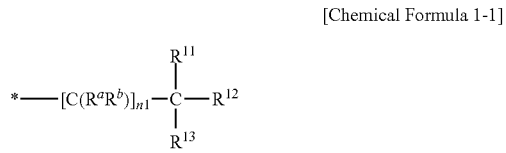

[Chemical Formula 1-1]

wherein, in Chemical Formula 1-1,
$R^a$ and $R^b$ is hydrogen, a halogen, a cyano group, or C1 to C6 alkyl group,
n1 is an integer of 0 to 10, and
$R^{11}$ to $R^{13}$ is hydrogen, a halogen, a cyano group, a C1 to C10 alkyl group, a C1 to C10 alkoxy group, a C2 to C10 alkenyl group, or a C2 to C10 alkynyl group, provided that at least two of $R^{11}$ to $R^{13}$ are a C1 to C10 alkyl group, a C1 to C10 alkoxy group, a C2 to C10 alkenyl group, or a C2 to C10 alkynyl group.

6. The fullerene derivative of claim 1, wherein
in Chemical Formula 1, at least one of $R^1$ to $R^3$ is a functional group including —O—, —S—, —S(=O)—, —S(=O)$_2$—, —C(=O)—, —C(=O)O—, —OC(=O)—, or a combination thereof, instead of at least one —C($R^c R^d$)— in Chemical Formula 1-2:

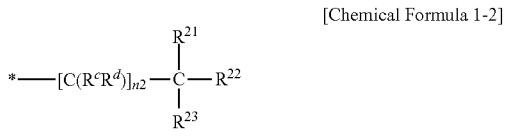

[Chemical Formula 1-2]

wherein, in Chemical Formula 1-2,
$R^c$ and $R^d$ is hydrogen, a halogen, a cyano group, a C1 to C6 alkyl group, a C1 to C6 alkoxy group, a C2 to C10 ether group, or a C2 to C10 ester group,
n2 is an integer of 2 to 10, and
$R^{21}$ to $R^{23}$ is hydrogen, a halogen, a cyano group, a C1 to C10 alkyl group, a C1 to C10 alkoxy group, a C2 to C10 alkenyl group, or a C2 to C10 alkynyl group, provided that at least two of $R^{11}$ to $R^{13}$ are a C1 to C10 alkyl group, a C1 to C10 alkoxy group, a C2 to C10 alkenyl group, or a C2 to C10 alkynyl group.

7. The fullerene derivative of claim 1, wherein
in Chemical Formula 1, at least one of $R^1$ to $R^3$ is an isopropyl group, an isobutyl group, an isopentyl group, an isohexyl group, an isoheptyl group, an isooctyl group, a t-butyl group, a t-pentyl group, a t-hexyl group, a neopentyl group, or a neohexyl group.

8. The fullerene derivative of claim 1, wherein the fullerene derivative exhibits three or more reduction peaks at −1.0 V to −2.0 V in the current-voltage curve line of cyclic-voltammetry (CV).

9. The fullerene derivative of claim 1, wherein the fullerene derivative has a LUMO energy level of about 2.6 eV to about 4.1 eV and a HOMO energy level of about 5.5 eV to about 6.9 eV.

10. The fullerene derivative of claim 1, wherein the fullerene derivative has an energy bandgap of 2.46 eV to about 2.56 eV.

11. The fullerene derivative of claim 1, wherein the fullerene derivative is a compound capable of being vacuum-deposited by sublimation.

12. The fullerene derivative of claim 8, wherein
a temperature at which a weight loss of 10% relative to an initial weight of the fullerene derivative occurs is less than or equal to about 460° C. during a thermogravimetric analysis at less than or equal to about 0.1 Pa, and a temperature at which 50% weight loss relative to the initial weight of the fullerene derivative occurs is less than or equal to about 500° C. during a thermogravimetric analysis at less than or equal to about 0.1 Pa.

13. The fullerene derivative of claim 1, wherein the fullerene core is C60, C70, C74, C76, or C78.

14. The fullerene derivative of claim 1, wherein the substituent represented by Chemical Formula 1 is represented by one of Chemical Formulae 2A to 4A:

[Chemical Formula 2A]

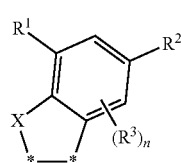

[Chemical Formula 2B]

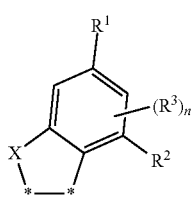

[Chemical Formula 3A]

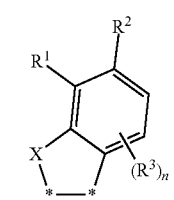

[Chemical Formula 3B]

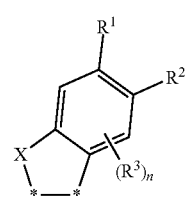

[Chemical Formula 3C]

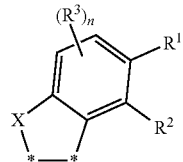

[Chemical Formula 4A]

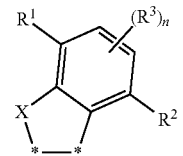

wherein in Chemical Formulae 2A to 4A,

X is S, $R^1$ to $R^3$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, a halogen, a cyano group, or a combination thereof, n is an integer of 1 or 2, and

*—* is a linking point with a fullerene core.

15. The fullerene derivative of claim 14, wherein in Chemical Formulae 2A to 4A, at least one of $R^1$ and $R^2$ is a linear substituent or a branched substituent, the linear substituent is selected from a substituted or unsubstituted C1 to C20 linear alkyl group, a substituted or unsubstituted C2 to C20 linear alkenyl group, a substituted or unsubstituted C2 to C20 linear alkynyl group, a substituted or unsubstituted C1 to C20 linear heteroalkyl group, a substituted or unsubstituted C2 to C20 linear heteroalkenyl group, a substituted or unsubstituted C2 to C20 linear heteroalkynyl group, or a combination thereof, and the branched substituent is selected from a substituted or unsubstituted C3 to C20 branched alkyl group, a substituted or unsubstituted C3 to C20 branched alkenyl group, a substituted or unsubstituted C3 to C20 branched alkynyl group, a substituted or unsubstituted C3 to C20 branched heteroalkyl group, a substituted or unsubstituted C3 to C20 branched heteroalkenyl group, a substituted or unsubstituted C3 to C20 branched heteroalkynyl group, or a combination thereof.

16. The fullerene derivative of claim 15, wherein in Chemical Formulae 2A to 4A, one of $R^1$ and $R^2$ is the linear substituent and the other of $R^1$ and $R^2$ is the branched substituent.

17. The fullerene derivative of claim 1, wherein the substituent represented by Chemical Formula 1 is represented by one of Chemical Formulae 5A to 7B:

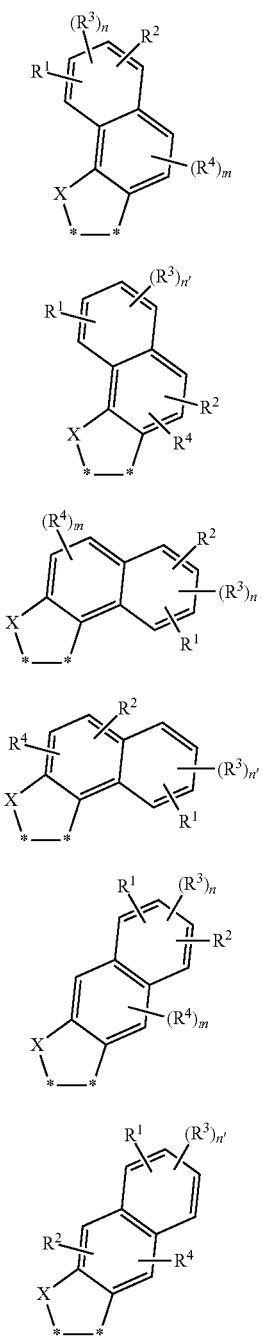

[Chemical Formula 5A]

[Chemical Formula 5B]

[Chemical Formula 6A]

[Chemical Formula 6B]

[Chemical Formula 7A]

[Chemical Formula 7B]

wherein, in Chemical Formulae 5A to 7B,

X is S, $R^1$ to $R^4$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C2 to C20 alkynyl group, a substituted or unsubstituted C2 to C20 heteroalkynyl group, halogen, a cyano group, or a combination thereof, n and m are independently an integer of 1 or 2, n' is an integer of 1 to 3, and

*—* is a linking point with a fullerene core.

18. The fullerene derivative of claim 17, wherein in Chemical Formulae 5A to 7B, at least one of $R^1$ and $R^2$ is a linear substituent or a branched substituent, the linear substituent is selected from a substituted or unsubstituted C1 to C20 linear alkyl group, a substituted or unsubstituted C2 to C20 linear alkenyl group, a substituted or unsubstituted C2 to C20 linear alkynyl group, a substituted or unsubstituted C1 to C20 linear heteroalkyl group, a substituted or unsubstituted C2 to C20 linear heteroalkenyl group, a substituted or unsubstituted C2 to C20 linear heteroalkynyl group, or a combination thereof, and the branched substituent is selected from a substituted or unsubstituted C3 to C20 branched alkyl group, a substituted or unsubstituted C3 to C20 branched alkenyl group, a substituted or unsubstituted C3 to C20 branched alkynyl group, a substituted or unsubstituted C3 to C20 branched heteroalkyl group, a substituted or unsubstituted C3 to C20 branched heteroalkenyl group, a substituted or unsubstituted C3 to C20 branched heteroalkynyl group, or a combination thereof.

19. The fullerene derivative of claim 18, wherein in Chemical Formulae 5A to 7B, one of $R^1$ and $R^2$ is the linear substituent and the other of $R^1$ and $R^2$ is the branched substituent.

20. A thin film comprising:

the fullerene derivative of claim 1.

21. The thin film of claim 20, wherein an extinction coefficient at a 450 nm wavelength of the thin film is smaller than an extinction coefficient at a 450 nm wavelength of other thin film including unsubstituted C60 fullerene.

22. The thin film of claim 21, wherein an absorption coefficient at a 450 nm wavelength of the thin film is less than or equal to about ½ of an absorption coefficient at a 450 nm wavelength of the other thin film including unsubstituted fullerene.

23. An organic photoelectric device comprising:

a first electrode and a second electrode facing each other, and an organic layer between the first electrode and the second electrode wherein the organic layer includes the fullerene derivative of claim 1.

24. An image sensor comprising:

the organic photoelectric device of claim 23.

25. An electronic device comprising:

the organic photoelectric device of claim 23.

26. The organic photoelectric device of claim 1, wherein in Chemical Formula 1,

R1 to R3 are independently hydrogen, deuterium, a substituted or unsubstituted C1 to C20 alkyl group, a substituted or unsubstituted C1 to C20 heteroalkyl group, a halogen, a cyano group, or a combination thereof.

27. The organic photoelectric device of claim 1, in Chemical Formula 1,

Ar is a benzene ring, and a, b, and c are 1.

* * * * *